US005770203A

United States Patent [19]
Burnette et al.

[11] Patent Number: 5,770,203
[45] Date of Patent: Jun. 23, 1998

[54] MODIFIED CHOLERA TOXIN BASED ON MUTAGENIZED SUBUNIT A

[75] Inventors: W. Neal Burnette, Thousand Oaks; Harvey R. Kaslow, Los Angeles, both of Calif.

[73] Assignees: Amgen Inc., Thousand Oaks; University of Southern California, Los Angeles, both of Calif.

[21] Appl. No.: 449,045

[22] Filed: May 24, 1995

Related U.S. Application Data

[62] Division of Ser. No. 271,222, Jul. 6, 1994, abandoned, which is a continuation of Ser. No. 694,733, May 2, 1991, abandoned.

[51] Int. Cl.$^6$ .......................... A61K 39/106; C12N 9/10; C07K 14/28
[52] U.S. Cl. .................... 424/190.1; 424/185.1; 424/261.1; 424/945; 424/832; 530/350; 435/193
[58] Field of Search ............................ 424/185.1, 261.1, 424/94.5, 832; 435/193; 530/350

[56] References Cited

U.S. PATENT DOCUMENTS 4,666,837  5/1987  Harford et al. ...................... 435/69.3

FOREIGN PATENT DOCUMENTS 0 125 228  11/1984  European Pat. Off. .

OTHER PUBLICATIONS

Cieplak et al., *Proc. Natl. Acad. Sci. USA*, vol. 85, pp. 4667–4671 (1988).

Sporecke et al., *J. Bacteriology*, vol. 157, No. 1, pp. 253–261 (1984).

Duffy et al., *Arch. Biochem. & Biophys.*, vol. 239, No. 2, pp. 549–555 (1985).

Jobling et al., *Abs. Ann. Meet. Am. Soc. Microbio.*, p. 59, B–205 (1991).

Xia et al., *Arch. Biochem. & Biophys.*, vol. 234, No. 2, pp. 363–370 (1984).

Brickman et al., *Abs. Ann. Meet. Am. Soc. Microbio.*, p. 62, B–192 (1989).

Honda et al., *Proc. Natl. Acad. Sci. USA*, vol. 76, No. 4, pp. 2052–2056 (1979).

Brickman et al., *Infec. & Immun.*, vol. 58, No. 12, pp. 4142–4144 (1990).

Locht et al., *Science*, vol. 232, pp. 1258–1264 (1986).

Tsuji et al., *J. Biol. Chem.*, vol. 265, No. 36, pp. 22520–22525 (1990).

*Primary Examiner*—Rebecca E. Prouty
*Assistant Examiner*—Gabriele E. Bugnisky
*Attorney, Agent, or Firm*—Richard J. Mazza; Ron Levy; Steven M. Odre

[57] ABSTRACT

The development of subunits and subunit analogs of the cholera exotoxin by recombinant DNA techniques provides vaccine products that can retain their biological activity and immunogenicity, and can confer protection against disease challenge. Genetically-engineered modifications of the subunits result in products that retain immunogenicity, yet are reduced in, or are essentially free of, enzymatic activity associated with toxin reactogenicity.

8 Claims, 12 Drawing Sheets

```
                                                          ┌→ mature A
    ┌→ preA                                               │
  1 ATGGTAAAGATAATATTTGTGTTTTTTATTTTCTTATCATCATTTTCATATGCA AAATGAT    60
    TACCATTTCTATTATAAACACAAAAAAATAATAAGAATAGTAAAAGTATACGT TTTACTA     -
    M   V   K   I   I   F   V   F   F   I   F   L   S   S   F   S   Y   A   N   D    -

Xba I
 61 GATAAGTTATATCGGGCAGATTCTAGACCTCCTGATGAATAAAGCAGTCAGGTGGTCTT    120
    CTATTCAATATAGCCCGTCTAAGATCTGGAGGACTACTTTATTTCGTCAGTCCACCAGAA     -
    D   K   L   Y   R   A   D   S   R   P   P   D   E   I   K   Q   S   G   G   L    -

Sca I                       Bcl I
121 ATGCCAAGAGGACAGAGTGAGTACTTTGACCGAGGTACTCAAATGAATATCAACTTTAT    180
    TACGGTTCTCCTGTCTCACTCATGAAACTGGCTCCATGAGTTTACTTATAGTTGAAATA     -
    M   P   R   G   Q   S   E   Y   F   D   R   G   T   Q   M   N   I   N   L   Y    -

181 GATCATGCAAGAGGAACTCAGACGGGATTTGTTAGGCACGATGATGGATATGTTTCCACC    240
    CTAGTACGTTCTCCTTGAGTCTGCCCTAAACAATCCGTGCTACTACCTATACAAAGGTGG     -
    D   H   A   R   G   T   Q   T   G   F   V   R   H   D   D   G   Y   V   S   T    -

241 TCAATTAGTTTGAGAAGTGCCCACTTAGTGGGTCAAACTATATTGTCTGGTCATTCTACT 300
    AGTTAATCAAACTCTTCACGGGTGAATCACCCAGTTTGATATAACAGACCAGTAAGATGA
    S  I  S  L  R  S  A  H  L  V  G  Q  T  I  L  S  G  H  S  T  -

A
                              f    N     T
                              l    s     a
                              H    p     q
                              I    H     H
                              I    I     I    I
301 TATTATTATATATGTTATAGCCACTGCACCCAACATGTTTAACGTTAATGATGTATTAGGG 360
    ATAATATATATACAATATCGGTGACGTGGGTTGTACAAATTGCAATTACTACATAATCCC
    Y  Y  Y  I  Y  V  I  A  T  A  P  N  M  F  N  V  N  D  V  L  G  -

361 GCATACAGTCCCTCATCCCAGATGAACAAGAAGTTTCTGCTTTAGGTGGGATTCCATACTCC 420
    CGTATGTCAGGGAGTAGGGTCTACTTGTTCTTCAAAGACGAAATCCACCCTAAGGTATGAGG
    A  Y  S  P  H  P  D  E  Q  E  V  S  A  L  G  G  I  P  Y  S
```

FIG.1A-1

```
                                                                  Tth111
                                                                  IIII
                 BstXI
421 CAAATATATGGATGGTATCGAGTTCATTTTGGGGTGCTTGATGAACAATTACATCGTAAT 480
     Q  I  Y  G  W  Y  R  V  H  F  G  V  L  D  E  Q  L  H  R  N  -
    GTTTATATACCTACCATAGCTCAAGTAAAACCCCACGAACTACTTGTTAATGTAGCATTA

BstXI                        BspMI
                              GsuI
481 AGGGGCTACAGAGATATTACAGTAACTTAGATATTGCTCCAGCAGATGGTTAT 540
     R  G  Y  R  D  R  Y  Y  S  N  L  D  I  A  P  A  A  D  G  Y  -
    TCCCCGATGTCTCTATCTATAAGTCATTGAATCTATAACGAGGTCGTCTACCAATA
                              KspI
                              63
                              2I
                              I

BspMI                        DsaI
541 GGATTGGCAGGTTTCCCCTCCCGGAGCATAGAGCTTGGAGGGAAGAGCCGTGGATTCATCAT 600
     G  L  A  G  F  P  P  E  H  R  A  W  R  E  E  P  W  I  H  H  -
    CCTAACCGTCCAAAGGGGAGGCCTCGTATCTCGAACCTCCCTTCTCGGCACCTAAGTAGTA
```

FIG.1A -2

```
                                                                    E
                                                                    c
                                                                    o
                                                                    R
                                                                    I
      ATGATTAAATTAAAATTTGGTGTGTTTTTTTACAGTTTTACTATCTTCAGCATATGCACAT
  1   TACTAATTTAATTTTAAACCACACAAAAAAATGTCAAAAATGATAGAAGTCGTATACGTGTA  60
      M  I  K  L  K  F  G  V  F  F  T  V  L  L  S  S  A  Y  A  T
   → PreB
                            S
                            s
                         ↓ p
      →Mature            I
         B
      GGAACACCCTCAAAATATTACTGATTTGTGTGCAGAATACCACACAACACACAAATATATACG
 61   CCTTGTGGAGTTTTATAATGACTAAACACACGTCTTATGGTGTGTTTGTGTTTATATATGC  120
      G  T  P  Q  N  I  T  D  L  C  A  E  Y  H  N  T  Q  I  Y
                                  A X
                                  c c
                                  c a
                                  I I
      CTAAATGATAAGATATTTTCGTATACAGAATCTCTAGCTGGAAAAAGAGAGAGATGGCTATC
121   GATTTACTATTCTATAAAAGCATATGTCTTAGAGATCGACCTTTTTCTCTCTACCGATAG   180
      L  N  D  K  I  F  S  Y  T  E  S  L  A  G  K  R  E  M  A  I
```

FIG. 1B

```
181 ATTACTTTTAAGAATGGTGCAATTTTTCAAGTAGAAGTACCAAGTAGTCAACATATAGAT 240
     I  T  F  K  N  G  A  I  F  Q  V  E  V  P  S  S  Q  H  I  D
    TAATGAAAATTCTTACCACGTTAAAAAGTTCATCTTCATGGTTCATCAGTTGTATATCTA
                                                          HinCII

241 TCACAAAAAAAGCGATTGAAAGGATGAAGGATACCCTGAGGATTGCATATCTTACTGAA 300
     S  Q  K  K  A  I  E  R  M  K  D  T  L  R  I  A  Y  L  T  E
    AGTGTTTTTTTCGCTAACTTTCCTACTTCCTATGGGACTCCTAACGTATAGAATGACTT
              AccI                                    Eco57I

301 GCTAAAGTCGAAAAGTTATGTGTATGGAATAATAAACGCCCTCATGCGATTGCCGCAATT 360
     A  K  V  E  K  L  C  V  W  N  N  K  T  P  H  A  I  A  A  I
    CGATTTCAGCTTTTCAATACACATACCTTATTATTTGCGGAGTACGCTAACGGCGTTAA
         End B

361 AGTATGGCAAATTAA 375
     S  M  A  N  *
    TCATACCGTTTAATT
```

FIG. 1B-1

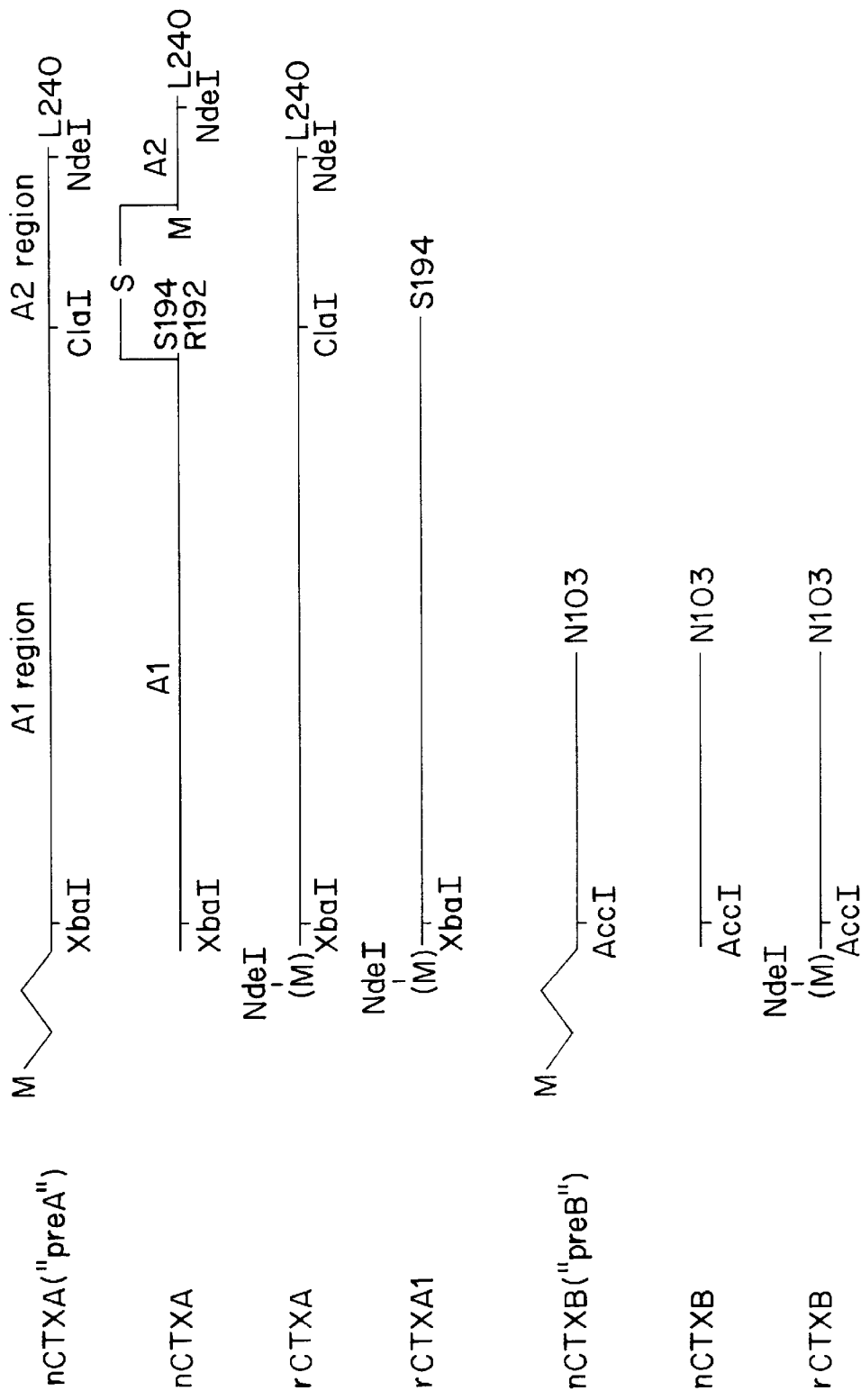

SEQUENCE LISTING ( 1 ) GENERAL INFORMATION:

( i i i ) NUMBER OF SEQUENCES: 34

( 2 ) INFORMATION FOR SEQ ID NO:1:

( i ) SEQUENCE CHARACTERISTICS:
        ( A ) LENGTH: 777 base pairs
        ( B ) TYPE: nucleic acid
        ( C ) STRANDEDNESS: double
        ( D ) TOPOLOGY: circular ( i i ) MOLECULE TYPE: cDNA ( i x ) FEATURE:
        ( A ) NAME/KEY: CDS
        ( B ) LOCATION: 1..777

( x i ) SEQUENCE DESCRIPTION: SEQ ID NO:1:

```
ATG GTA AAG ATA ATA TTT GTG TTT TTT ATT TTC TTA TCA TCA TTT TCA    48
Met Val Lys Ile Ile Phe Val Phe Phe Ile Phe Leu Ser Ser Phe Ser
 1               5                  10                  15

TAT GCA AAT GAT GAT AAG TTA TAT CGG GCA GAT TCT AGA CCT CCT GAT    96
Tyr Ala Asn Asp Asp Lys Leu Tyr Arg Ala Asp Ser Arg Pro Pro Asp
             20                  25                  30

GAA ATA AAG CAG TCA GGT GGT CTT ATG CCA AGA GGA CAG AGT GAG TAC   144
Glu Ile Lys Gln Ser Gly Gly Leu Met Pro Arg Gly Gln Ser Glu Tyr
         35                  40                  45

TTT GAC CGA GGT ACT CAA ATG AAT ATC AAC CTT TAT GAT CAT GCA AGA   192
Phe Asp Arg Gly Thr Gln Met Asn Ile Asn Leu Tyr Asp His Ala Arg
     50                  55                  60

GGA ACT CAG ACG GGA TTT GTT AGG CAC GAT GAT GGA TAT GTT TCC ACC   240
Gly Thr Gln Thr Gly Phe Val Arg His Asp Asp Gly Tyr Val Ser Thr
 65                  70                  75                  80

TCA ATT AGT TTG AGA AGT GCC CAC TTA GTG GGT CAA ACT ATA TTG TCT   288
Ser Ile Ser Leu Arg Ser Ala His Leu Val Gly Gln Thr Ile Leu Ser
                 85                  90                  95

GGT CAT TCT ACT TAT TAT ATA TAT GTT ATA GCC ACT GCA CCC AAC ATG   336
Gly His Ser Thr Tyr Tyr Ile Tyr Val Ile Ala Thr Ala Pro Asn Met
            100                 105                 110

TTT AAC GTT AAT GAT GTA TTA GGG GCA TAC AGT CCT CAT CCA GAT GAA   384
Phe Asn Val Asn Asp Val Leu Gly Ala Tyr Ser Pro His Pro Asp Glu
        115                 120                 125

CAA GAA GTT TCT GCT TTA GGT GGG ATT CCA TAC TCC CAA ATA TAT GGA   432
Gln Glu Val Ser Ala Leu Gly Gly Ile Pro Tyr Ser Gln Ile Tyr Gly
    130                 135                 140

TGG TAT CGA GTT CAT TTT GGG GTG CTT GAT GAA CAA TTA CAT CGT AAT   480
Trp Tyr Arg Val His Phe Gly Val Leu Asp Glu Gln Leu His Arg Asn
145                 150                 155                 160
```

| | | | | | | | | | | | | | | | | |
|---|---|---|---|---|---|---|---|---|---|---|---|---|---|---|---|---|
| AGG | GGC | TAC | AGA | GAT | AGA | TAT | TAC | AGT | AAC | TTA | GAT | ATT | GCT | CCA | GCA | 528 |
| Arg | Gly | Tyr | Arg | Asp | Arg | Tyr | Tyr | Ser | Asn | Leu | Asp | Ile | Ala | Pro | Ala | |
| | | | | 165 | | | | | 170 | | | | | 175 | | |
| GCA | GAT | GGT | TAT | GGA | TTG | GCA | GGT | TTC | CCT | CCG | GAG | CAT | AGA | GCT | TGG | 576 |
| Ala | Asp | Gly | Tyr | Gly | Leu | Ala | Gly | Phe | Pro | Pro | Glu | His | Arg | Ala | Trp | |
| | | | 180 | | | | | 185 | | | | | 190 | | | |
| AGG | GAA | GAG | CCG | TGG | ATT | CAT | CAT | GCA | CCG | CCG | GGT | TGT | GGG | AAT | GCT | 624 |
| Arg | Glu | Glu | Pro | Trp | Ile | His | His | Ala | Pro | Pro | Gly | Cys | Gly | Asn | Ala | |
| | | 195 | | | | | 200 | | | | | 205 | | | | |
| CCA | AGA | TCA | TCG | ATG | AGT | AAT | ACT | TGC | GAT | GAA | AAA | ACC | CAA | AGT | CTA | 672 |
| Pro | Arg | Ser | Ser | Met | Ser | Asn | Thr | Cys | Asp | Glu | Lys | Thr | Gln | Ser | Leu | |
| | 210 | | | | | 215 | | | | | 220 | | | | | |
| GGT | GTA | AAA | TTC | CTT | GAC | GAA | TAC | CAA | TCT | AAA | GTT | AAA | AGA | CAA | ATA | 720 |
| Gly | Val | Lys | Phe | Leu | Asp | Glu | Tyr | Gln | Ser | Lys | Val | Lys | Arg | Gln | Ile | |
| 225 | | | | | 230 | | | | | 235 | | | | | 240 | |
| TTT | TCA | GGC | TAT | CAA | TCT | GAT | ATT | GAT | ACA | CAT | AAT | AGA | ATT | AAG | GAT | 768 |
| Phe | Ser | Gly | Tyr | Gln | Ser | Asp | Ile | Asp | Thr | His | Asn | Arg | Ile | Lys | Asp | |
| | | | | 245 | | | | | 250 | | | | | 255 | | |
| GAA | TTA | TGA | | | | | | | | | | | | | | 777 |
| Glu | Leu | * | | | | | | | | | | | | | | |

( 2 ) INFORMATION FOR SEQ ID NO:2:

( i ) SEQUENCE CHARACTERISTICS:
        ( A ) LENGTH: 258 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| | | | | | | | | | | | | | | | |
|---|---|---|---|---|---|---|---|---|---|---|---|---|---|---|---|
| Met | Val | Lys | Ile | Ile | Phe | Val | Phe | Phe | Ile | Phe | Leu | Ser | Ser | Phe | Ser |
| 1 | | | | 5 | | | | | 10 | | | | | 15 | |
| Tyr | Ala | Asn | Asp | Asp | Lys | Leu | Tyr | Arg | Ala | Asp | Ser | Arg | Pro | Pro | Asp |
| | | | 20 | | | | | 25 | | | | | 30 | | |
| Glu | Ile | Lys | Gln | Ser | Gly | Gly | Leu | Met | Pro | Arg | Gly | Gln | Ser | Glu | Tyr |
| | | | 35 | | | | | 40 | | | | | 45 | | |
| Phe | Asp | Arg | Gly | Thr | Gln | Met | Asn | Ile | Asn | Leu | Tyr | Asp | His | Ala | Arg |
| | | 50 | | | | | 55 | | | | | 60 | | | |
| Gly | Thr | Gln | Thr | Gly | Phe | Val | Arg | His | Asp | Asp | Gly | Tyr | Val | Ser | Thr |
| 65 | | | | | 70 | | | | | 75 | | | | | 80 |
| Ser | Ile | Ser | Leu | Arg | Ser | Ala | His | Leu | Val | Gly | Gln | Thr | Ile | Leu | Ser |
| | | | | 85 | | | | | 90 | | | | | 95 | |
| Gly | His | Ser | Thr | Tyr | Tyr | Ile | Tyr | Val | Ile | Ala | Thr | Ala | Pro | Asn | Met |
| | | | 100 | | | | | 105 | | | | | 110 | | |
| Phe | Asn | Val | Asn | Asp | Val | Leu | Gly | Ala | Tyr | Ser | Pro | His | Pro | Asp | Glu |
| | | 115 | | | | | 120 | | | | | 125 | | | |
| Gln | Glu | Val | Ser | Ala | Leu | Gly | Gly | Ile | Pro | Tyr | Ser | Gln | Ile | Tyr | Gly |
| | 130 | | | | | 135 | | | | | 140 | | | | |
| Trp | Tyr | Arg | Val | His | Phe | Gly | Val | Leu | Asp | Glu | Gln | Leu | His | Arg | Asn |
| 145 | | | | | 150 | | | | | 155 | | | | | 160 |
| Arg | Gly | Tyr | Arg | Asp | Arg | Tyr | Tyr | Ser | Asn | Leu | Asp | Ile | Ala | Pro | Ala |
| | | | | 165 | | | | | 170 | | | | | 175 | |
| Ala | Asp | Gly | Tyr | Gly | Leu | Ala | Gly | Phe | Pro | Pro | Glu | His | Arg | Ala | Trp |
| | | | 180 | | | | | 185 | | | | | 190 | | |
| Arg | Glu | Glu | Pro | Trp | Ile | His | His | Ala | Pro | Pro | Gly | Cys | Gly | Asn | Ala |
| | | 195 | | | | | 200 | | | | | 205 | | | |
| Pro | Arg | Ser | Ser | Met | Ser | Asn | Thr | Cys | Asp | Glu | Lys | Thr | Gln | Ser | Leu |

```
                          210                       215                       220
Gly  Val  Lys  Phe  Leu  Asp  Glu  Tyr  Gln  Ser  Lys  Val  Lys  Arg  Gln  Ile
225                      230                      235                       240

Phe  Ser  Gly  Tyr  Gln  Ser  Asp  Ile  Asp  Thr  His  Asn  Arg  Ile  Lys  Asp
                    245                      250                      255

Glu  Leu
```

( 2 ) INFORMATION FOR SEQ ID NO:3:

( i ) SEQUENCE CHARACTERISTICS:
        ( A ) LENGTH: 375 base pairs
        ( B ) TYPE: nucleic acid
        ( C ) STRANDEDNESS: double
        ( D ) TOPOLOGY: circular ( i i ) MOLECULE TYPE: cDNA ( i x ) FEATURE:
        ( A ) NAME/KEY: CDS
        ( B ) LOCATION: 1..375

( x i ) SEQUENCE DESCRIPTION: SEQ ID NO:3:

```
ATG  ATT  AAA  TTA  AAA  TTT  GGT  GTT  TTT  TTT  ACA  GTT  TTA  CTA  TCT  TCA      48
Met  Ile  Lys  Leu  Lys  Phe  Gly  Val  Phe  Phe  Thr  Val  Leu  Leu  Ser  Ser
  1                    5                       10                       15

GCA  TAT  GCA  CAT  GGA  ACA  CCT  CAA  AAT  ATT  ACT  GAT  TTG  TGT  GCA  GAA      96
Ala  Tyr  Ala  His  Gly  Thr  Pro  Gln  Asn  Ile  Thr  Asp  Leu  Cys  Ala  Glu
                     20                       25                       30

TAC  CAC  AAC  ACA  CAA  ATA  TAT  ACG  CTA  AAT  GAT  AAG  ATA  TTT  TCG  TAT     144
Tyr  His  Asn  Thr  Gln  Ile  Tyr  Thr  Leu  Asn  Asp  Lys  Ile  Phe  Ser  Tyr
           35                       40                       45

ACA  GAA  TCT  CTA  GCT  GGA  AAA  AGA  GAG  ATG  GCT  ATC  ATT  ACT  TTT  AAG     192
Thr  Glu  Ser  Leu  Ala  Gly  Lys  Arg  Glu  Met  Ala  Ile  Ile  Thr  Phe  Lys
 50                       55                       60

AAT  GGT  GCA  ATT  TTT  CAA  GTA  GAA  GTA  CCA  AGT  AGT  CAA  CAT  ATA  GAT     240
Asn  Gly  Ala  Ile  Phe  Gln  Val  Glu  Val  Pro  Ser  Ser  Gln  His  Ile  Asp
 65                       70                       75                       80

TCA  CAA  AAA  AAA  GCG  ATT  GAA  AGG  ATG  AAG  GAT  ACC  CTG  AGG  ATT  GCA     288
Ser  Gln  Lys  Lys  Ala  Ile  Glu  Arg  Met  Lys  Asp  Thr  Leu  Arg  Ile  Ala
                     85                       90                       95

TAT  CTT  ACT  GAA  GCT  AAA  GTC  GAA  AAG  TTA  TGT  GTA  TGG  AAT  AAT  AAA     336
Tyr  Leu  Thr  Glu  Ala  Lys  Val  Glu  Lys  Leu  Cys  Val  Trp  Asn  Asn  Lys
              100                      105                      110

ACG  CCT  CAT  GCG  ATT  GCC  GCA  ATT  ACT  ATG  GCA  AAT  TAA                     375
Thr  Pro  His  Ala  Ile  Ala  Ala  Ile  Thr  Met  Ala  Asn   *
           115                      120                      125
```

( 2 ) INFORMATION FOR SEQ ID NO:4:

( i ) SEQUENCE CHARACTERISTICS:
        ( A ) LENGTH: 124 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Met  Ile  Lys  Leu  Lys  Phe  Gly  Val  Phe  Phe  Thr  Val  Leu  Leu  Ser  Ser
  1                    5                       10                       15

Ala  Tyr  Ala  His  Gly  Thr  Pro  Gln  Asn  Ile  Thr  Asp  Leu  Cys  Ala  Glu
                     20                       25                       30

Tyr  His  Asn  Thr  Gln  Ile  Tyr  Thr  Leu  Asn  Asp  Lys  Ile  Phe  Ser  Tyr
           35                       40                       45
```

| Thr | Glu | Ser | Leu | Ala | Gly | Lys | Arg | Glu | Met | Ala | Ile | Ile | Thr | Phe | Lys |
|     | 50  |     |     |     |     | 55  |     |     |     |     | 60  |     |     |     |     |

| Asn | Gly | Ala | Ile | Phe | Gln | Val | Glu | Val | Pro | Ser | Gln | His | Ile | Asp |
| 65  |     |     |     |     | 70  |     |     |     |     | 75  |     |     |     | 80  |

| Ser | Gln | Lys | Lys | Ala | Ile | Glu | Arg | Met | Lys | Asp | Thr | Leu | Arg | Ile | Ala |
|     |     |     |     | 85  |     |     |     |     | 90  |     |     |     |     | 95  |     |

| Tyr | Leu | Thr | Glu | Ala | Lys | Val | Glu | Lys | Leu | Cys | Val | Trp | Asn | Asn | Lys |
|     |     |     | 100 |     |     |     |     | 105 |     |     |     |     | 110 |     |     |

| Thr | Pro | His | Ala | Ile | Ala | Ala | Ile | Thr | Met | Ala | Asn |
|     |     | 115 |     |     |     |     | 120 |     |     |     |     | 125 |

( 2 ) INFORMATION FOR SEQ ID NO:5:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:5:

CATCGATTCT AG      12

( 2 ) INFORMATION FOR SEQ ID NO:6:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:6:

AATTCTAGAA TCGATGACGT      20

( 2 ) INFORMATION FOR SEQ ID NO:7:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:7:

CGATTTGATT      10

( 2 ) INFORMATION FOR SEQ ID NO:8:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:8:

CTAGAATCAA AT      12

( 2 ) INFORMATION FOR SEQ ID NO:9:

( i ) SEQUENCE CHARACTERISTICS:
        ( A ) LENGTH: 46 base pairs (B) TYPE: nucleic acid
(C) STRANDEDNESS: single
(D) TOPOLOGY: linear (i i) MOLECULE TYPE: cDNA (x i) SEQUENCE DESCRIPTION: SEQ ID NO:9:

CTAGAAGGAA GGAATAACAT ATGGTTAACG CGTTGGAATT CGGTAC 46

(2) INFORMATION FOR SEQ ID NO:10:

(i) SEQUENCE CHARACTERISTICS:
(A) LENGTH: 38 base pairs
(B) TYPE: nucleic acid
(C) STRANDEDNESS: single
(D) TOPOLOGY: linear (i i) MOLECULE TYPE: cDNA (x i) SEQUENCE DESCRIPTION: SEQ ID NO:10:

CGAATTCCAA CGCGTTAACC ATATGTTATT CCTTCCTT 38

(2) INFORMATION FOR SEQ ID NO:11:

(i) SEQUENCE CHARACTERISTICS:
(A) LENGTH: 32 base pairs
(B) TYPE: nucleic acid
(C) STRANDEDNESS: single
(D) TOPOLOGY: linear (i i) MOLECULE TYPE: cDNA (x i) SEQUENCE DESCRIPTION: SEQ ID NO:11:

TATGAATGAT GATAAGTTAT ATCGGGCAGA TT 32

(2) INFORMATION FOR SEQ ID NO:12:

(i) SEQUENCE CHARACTERISTICS:
(A) LENGTH: 34 base pairs
(B) TYPE: nucleic acid
(C) STRANDEDNESS: single
(D) TOPOLOGY: linear (i i) MOLECULE TYPE: cDNA (x i) SEQUENCE DESCRIPTION: SEQ ID NO:12:

CTAGAATCTG CCCGATATAA CTTATCATCA TTCA 34

(2) INFORMATION FOR SEQ ID NO:13:

(i) SEQUENCE CHARACTERISTICS:
(A) LENGTH: 20 base pairs
(B) TYPE: nucleic acid
(C) STRANDEDNESS: single
(D) TOPOLOGY: linear (i i) MOLECULE TYPE: cDNA (x i) SEQUENCE DESCRIPTION: SEQ ID NO:13:

GTGGAATTCG GTACCATGGA 20

(2) INFORMATION FOR SEQ ID NO:14:

(i) SEQUENCE CHARACTERISTICS:
(A) LENGTH: 20 base pairs
(B) TYPE: nucleic acid
(C) STRANDEDNESS: single
(D) TOPOLOGY: linear (i i) MOLECULE TYPE: cDNA ( x i ) SEQUENCE DESCRIPTION: SEQ ID NO:14:

GTGGAATTCG GTACCATGGA 20

( 2 ) INFORMATION FOR SEQ ID NO:15:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:15:

TATGACACCT CAAAAT 16

( 2 ) INFORMATION FOR SEQ ID NO:16:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:16:

ATTTTGATTT GTCA 14

( 2 ) INFORMATION FOR SEQ ID NO:17:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:17:

TATGAATGAT GATAAGTTAT ATAAGGCAGA TT 32

( 2 ) INFORMATION FOR SEQ ID NO:18:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:18:

CTAGAATCTG CCTTATATAA CTTATCATCA TTCA 34

( 2 ) INFORMATION FOR SEQ ID NO:19:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:19:

TATGAATGAT GATAAGTTAT TCCGGGCAGA TT 32

( 2 ) INFORMATION FOR SEQ ID NO:20:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:20:

CTAGAATCTG CCCGGAATAA CTTATCATCA TTCA    34

( 2 ) INFORMATION FOR SEQ ID NO:21:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:21:

TATGAATGAT GATAAGTTAT ATCGGGCAGA AT    32

( 2 ) INFORMATION FOR SEQ ID NO:22:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:22:

CTAGATTCTG CCCGATATAA CTTATCATCA TTCA    34

( 2 ) INFORMATION FOR SEQ ID NO:23:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:23:

CGTGGATTCA TCATGCACCG CAGGGTTGTG GGAATGCTCC AAGATCATCG    50

( 2 ) INFORMATION FOR SEQ ID NO:24:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:24:

CGTGGATTCA TCATGCACCG CAGGGTTGTG GGAATGCTCC AAGATCATCG    50

( 2 ) INFORMATION FOR SEQ ID NO:25:

( i ) SEQUENCE CHARACTERISTICS:
        ( A ) LENGTH: 50 base pairs (B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:25:

CGTGGATTCA TCATGCACCG CCGGGTGCAG GGAATGCTCC AAGATCATCG 50

(2) INFORMATION FOR SEQ ID NO:26:

(i) SEQUENCE CHARACTERISTICS:
(A) LENGTH: 50 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:26:

AGCTTCTACG ATGATCTTGG AGCATTCCCT GCACCCGGCG GTGCATGATG 50

(2) INFORMATION FOR SEQ ID NO:27:

(i) SEQUENCE CHARACTERISTICS:
(A) LENGTH: 15 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:27:

CGTGGTAATG ATAGA 15

(2) INFORMATION FOR SEQ ID NO:28:

(i) SEQUENCE CHARACTERISTICS:
(A) LENGTH: 15 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:28:

AGCTTCTATC ATTAC 15

(2) INFORMATION FOR SEQ ID NO:29:

(i) SEQUENCE CHARACTERISTICS:
(A) LENGTH: 23 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:29:

CCTTTATGAT AACGCAAGAG GAA 23

(2) INFORMATION FOR SEQ ID NO:30:

(i) SEQUENCE CHARACTERISTICS:
(A) LENGTH: 23 base pairs
(B) TYPE: nucleic acid
(C) STRANDEDNESS: single
(D) TOPOLOGY: linear (ii) MOLECULE TYPE: cDNA ( x i ) SEQUENCE DESCRIPTION: SEQ ID NO:30:

GAGAAGTGCC AACTTAGTGG GTC 23

( 2 ) INFORMATION FOR SEQ ID NO:31:

( i ) SEQUENCE CHARACTERISTICS:
( A ) LENGTH: 23 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:31:

AGATGAACAA CAGGTTTCTG CTT 23

( 2 ) INFORMATION FOR SEQ ID NO:32:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:32:

GGGGCTACAA GGATAGATAT 20

( 2 ) INFORMATION FOR SEQ ID NO:33:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:33:

CGTAATAGGC GGCCGCA 17

( 2 ) INFORMATION FOR SEQ ID NO:34:

( i ) SEQUENCE CHARACTERISTICS:
( A ) LENGTH: 19 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:34:

AGCTTGCGGC CGCCTATTA 19

MODIFIED CHOLERA TOXIN BASED ON MUTAGENIZED SUBUNIT A

This application is a divisional application of prior application Ser. No. 08/271,222, filed Jul. 6, 1994, abandoned, which in turn is a continuation application of prior application Ser. no. 07/694,733, filed May 2, 1991, abandoned.

BACKGROUND OF THE INVENTION

1. Field of the Invention

The present invention relates to the recombinant expression of analog subunits of cholera exotoxin, and to vaccines based on such analogs. More particularly, genetically engineered modifications of the exotoxin provide analogs of cholera toxin having the capability to elicit a protective response with reduced or essentially no catalytic activity which can contribute to the reactogenicity of cholera vaccines.

2. Description of the Art

The term "cholera" refers to the disease caused by infection with the etiologic agent *Vibrio cholerae*, most commonly occurring in geographical areas where poor hygienic conditions prevail. Cholera remains a major cause of morbidity and mortality in many parts of the world(1,2). Experience has shown that contraction of the disease usually confers long-lasting protection against subsequent exposure to the etiologic agent(3). Consequently, considerable effort has been devoted to the development of a vaccine that would be similarly protective. A parenteral whole cell cholera vaccine has been produced, but some no longer regard it as useful, particularly for young children who are at greatest risk from the disease(1).

As for many other infectious diseases, a biological exotoxin (in this case, "cholera toxin" or "CTX") encoded by the genome of the infectious agent and secreted by it, contributes significantly to the ability of the microorganism to colonize the infected host(4). Moreover, exposure to the toxin causes severe diarrhea and vomiting which result in dehydration, a life-threatening condition of the disease(3,5). These experiences suggest that a vaccine which elicits an immunologic response (e.g., antibodies) sufficient to neutralize the toxin would thus significantly help to prevent or reduce bacterial colonization and attendant symptoms such as diarrhea and vomiting. Thus, substantial effort has been applied toward developing a vaccine containing a non-toxic analog of the toxin, i.e., a "toxoid"(1,3-13). It is known that cholera toxin is a multi-subunit macromolecule consisting of a subunit termed "A", containing a catalytic region called "A1" which ADP-ribosylates G-proteins in target cells, and a "B" oligomer which binds the holotoxin to the target cells(6). Non-toxic analogs of cholera toxin have been produced for purposes of vaccine development by various means. These methods include chemical treatment of the holotoxin or toxin subunits, deletion of the A subunit and use of the remaining B oligomer, and synthesis or isolation of peptide fragments of toxin subunits(l,3-13).

In recent years, efforts have turned toward the development of oral vaccines, with two approaches apparently having received the most attention. One of these approaches is based on the use of killed *V. cholerae* (i.e., chemically- or heat-inactivated), alone, or supplemented with the B oligomer of cholera toxin(1,11,12). This approach has been found to produce incomplete protection, particularly in young children(12). The other approach involves the use of living, but attenuated, strains of *V. cholerae* which fail to produce the A1 subunit of the toxin(13). Vaccines of this kind have provided greater levels of protection, but until recently have also been associated with unacceptable intestinal side-effects. A recently-developed vaccine based on *V. cholerae* strain CVD 103-HgR, in which the gene encoding the A subunit is omitted, appears to be better tolerated, at least in adults(13). However, to our knowledge, this vaccine has not been tested in children or in large-scale clinical trials.

Recent studies on the nature of cholera toxin have provided insights concerning its structure that may have application in vaccine development based on a recombinant approach. It is known that naturally-ocurring subunit A is synthesized in *V. cholerae* as a preprotein(14), which is subsequently cleaved to proteolytically remove a signal peptide sequence of approximately 2,160 kDa. Further post-translational processing yields an amino-terminal polypeptide of approximately 21,817 kDa (subunit A1) and a carboxyl-terminal polypeptide of approximately 5,398 kDa (subunit A2), which are linked by a disulfide bridge(6,15, 16); reduction of the disulfide bond is believed necessary for catalysis of the ADP-ribosyltransferase reaction (6,15,16). Likewise, the B subunit is synthesized as a preprotein which is subsequently cleaved by protease to remove a signal peptide. The genes, or cistronic elements, for the A1, A2 and B subunits of cholera toxin have all been fully sequenced and described in the literature(16).

BRIEF DESCRIPTION OF THE FIGURES

FIG. 1B is the DNA sequence (SEQ ID NO: 1) of the cistronic element encoding the B subunit of CTX. The corresponding amino acid sequence (SEQ ID NO: 4) is also shown. Initiation and termination codons and proposed cleavage sites are likewise shown. Interestingly, the region of DNA in the operon encoding the termination of A2 and the initiation of B overlap; these two proteins, however, are in different reading frames.

SUMMARY OF THE INVENTION

The present invention provides a recombinant DNA molecule, at least a portion of which encodes an analog of the catalytic subunit of cholera toxin having reduced enzymatic activity, such activity generally accepted to be associated with vaccine reactogenicity. More specifically, site specific mutagenesis, as described herein, results in analogs of the A and A1 subunits which, compared to the native toxin counterparts, exhibit a significant reduction in catalytic function as measured by ADP-ribosyltransferase activity.

Figures 1, 1A, 2, 3:
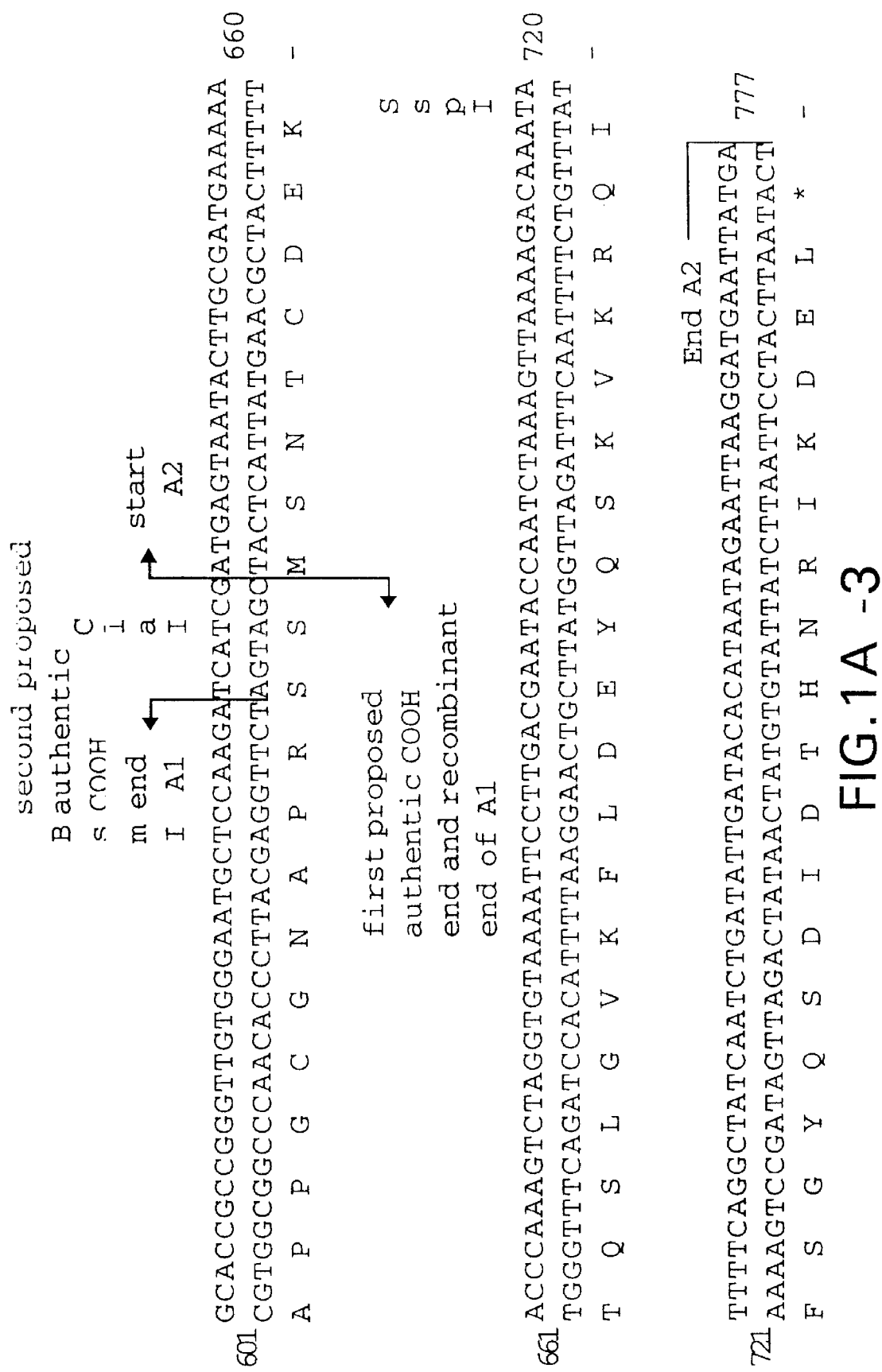
FIG. 1A is the DNA (SEQ ID NO: 1) sequencer of the cistronic element encoding the A subunit of CTX from the prior art. The single-letter amino acid sequence (SEQ ID NO: 2) beneath the DNA sequence indicates the proposed open reading frame for the A polypeptide. Subregions are also indicated, showing the start of the signal peptide (pre-A), A1, two proposed sites for carboxyl-terminal processing of A1, and the proposed start and termination of A2. It should be noted that the literature provides inconclusive evidence as to the exact location of the carboxyl terminus of A1(16,17).
FIG. 2 shows schematic structures for the preprotein and processed protein forms of the A and B subunits of native CTX and the forms of the recombinant subunits. The "squiggle" at the amino termini of the preprotein species represents the signal peptide which is removed by *V. cholerae*. "M" indicates an amino terminal methionine residue; "(M)" indicates that this is a heterologous (non-native) residue residing at the amino terminus of the mature recombinant CTXA and CTXA1 subunits, and analogs thereof; amino acid sequence data indicates that the heterologous methionine residue is not substantially cleaved from the recombinant polypeptide by cellular methionine amino-peptidase. "S" indicates the sulfur moiety involved in a disulfide linkage between cysteine residues. Other selected amino acids are indicated by their standard single-letter codes, with their position within the polypeptides indicated. Selected restriction enzyme cleavage sites for the encoding DNA sequences are indicated on the encoded polypeptide with their standard three-letter codes. Native ("n") CTXA is believed to be synthesized in *V. cholerae* as a preprotein ("pre-A"), containing an amino-terminal signal sequence. Post-translational processing results in cleavage of the signal to yield mature CTXA. Perhaps simultaneously, a small portion of the carboxyl terminus is also cleaved proteolytically. The larger A fragment (CTXA1) and the smaller carboxyl-terminal A fragment (CTXA2) are held together after cleavage by a disulfide bridge between the single cysteine residue in each fragment. The literature possesses conflicting reports as to the location of the terminus of CTXA1 (either $Arg^{192}$ or $Ser^{194}$); CTXA2 is believed to begin with $Met^{195}$. Native ("n") CTXB is also synthesized with an amino-terminal signal sequence that is subsequently processed by protease. Interestingly, the region of the CTXB cistronic element encoding its amino terminus overlaps with the CTXA cistronic element encoding its carboxyl terminus; the coding sequences, however, are in different reading frames(16). Recombinant ("r") CTXA was synthesized in *E. coli* under control of an optimized expression vector. An oligonucleotide linker (NdeI-XbaI) was used for cloning of the left-hand end of the DNA element, substituting an initiating methionine codon for the signal peptide-encoded sequence. The A2 region was not removed from A1 in the recombinant *E. coli*. A similar left-hand cloning strategy was used for CTXB, except an NdeI-AccI fragment was used to substitute the methionine initiation codon for its signal peptide-encoded sequence. Recombinant CTXA1 was synthesized to mimic native, reduced CTXA1. In this regard, an oligonucleotide linker at the right-hand end was used to substitute a termination codon for the A2 sequence such that A1 terminates at $Ser^{194}$, one of the two proposed cleavage sites in native CTXA1. Termination at $Arg^{192}$ can also be easily accomplished using the same linker strategy. As previously noted, the amino terminal methionines of the recombinant CTXA and CTXA1 molecules, and their analogs, are not believed to be substantially removed by nascent *E. coli* methionine aminopeptidase.
FIG. 3 is the SDS-PAGE of native and recombinant CTX subunits. Recombinant CTXA, CTXA1, the $Arg^7 \rightarrow Lys$ analogs of recombinant CTXA and CTXA1, and recombinant CTXB were synthesized in *E. coli* and inclusion bodies prepared as described in the text. The inclusion body preparations, as well as purified commercial-grade native CTX, CTXA, and CTXB, were solubilized and subjected to SDS-PAGE under reducing conditions. Lane 1, native CTX; lane 2, rCTXA/A7; lane 3, rCTXA $Arg^7 \rightarrow Lys$ analog (rCTXA/L7); lane 4, rCTXA1/A7; lane 5, rCTXAl $Arg^7 \rightarrow Lys$ analog (rCTXAl/L7); lane 6, rCTXB; lane 7, native CTXB; lane 8, native CTXA (only CTXA1 is visualized). Subsequent to electrophoresis, the gel was stained with Coomassie Brilliant Blue R250 and then destained to reveal the stain-retaining polypeptides.
Figure 3:
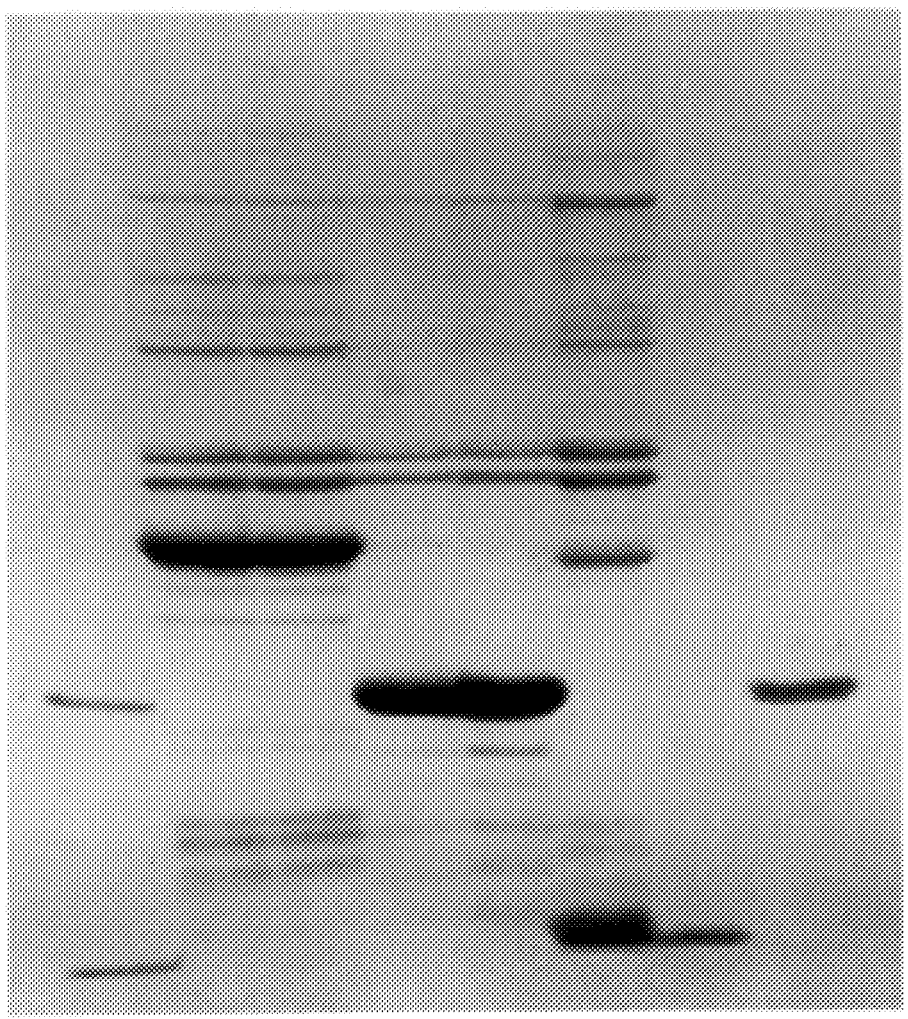

The term "catalytic subunit of cholera toxin" used in this disclosure refers to both the A region of cholera toxin and the A1 subregion, as depicted in FIGS. 1A and 2. These regions of the cholera toxin macromolecule are known to possess ADP-ribosyltransferase catalytic activity(6). This enzyme is a complex of two sub-activities: an NAD glycohydrolase activity which cleaves NAD into nicotinamide and ADP-ribose, and a transferase activity which transfers the ADP-ribose to the G protein substrate. Measurements of the ADP-ribosyltransferase activity in this disclosure represent a summation of both activities. The present invention comprehends mutagenesized versions of these A and A1 polypeptides, and analogs or derivatives of such polypeptides, which in their native forms are sources of catalytic activity within the cholera toxin multimer.

The genetically-engineered analogs of cholera toxin, which are a product of this invention, provide recombinant DNA-derived materials suitable for use in vaccines for the prevention of cholera disease. The A and A1 subunit analogs can be used alone or in combination with B oligomer in a toxoid-based vaccine, or phenotypically expressed by variants of *V. cholerae*, or phenotypically expressed under the genetic control of other immunizing vectors. It should be noted that the analog A and A1 subunits of this invention are utilizable by themselves as antigenic agents in a vaccine because they may contain important protective epitopes. However, the use of these analogs in association with B subunits may be more desirable. The B oligomer contains neutralizing epitopes useful for eliciting immunoprotection (1,3,5). Association of the A subunit with the B oligomer may lead to a more effective immunogenic response against the B oligomer. The B oligomer can be purified from *V. cholerae* or, alternatively, can be derived recombinantly in a manner similar to the A and A1 subunits by expression in *E. coli* or other recombinant hosts, including other bacterial organisms (e.g., *Salmonella typhimurium* or *typhi*, Bacillus sp.), yeast (e.g., *S. cerevisiae*), and viruses (e.g., vaccinia and adenoviruses).

Mutagenesis in accordance with this description enables production of mutants varying in diminished catalytic activity, ranging from variants which exhibit attenuated activity to those which are essentially free of such activity (i.e., less than 5%). This flexibility in approach is desirable because attenuation, rather than elimination, of catalytic activity may be helpful in providing a greater degree of and/or longer-lasting, protective response. Moreover, because of their diminished enzymatic activity, the analog subunits provided by this invention are expected to be less reactogenic.

DETAILED DESCRIPTION

The present invention provides high-level, direct recombinant expression of all CTX subunits necessary for vaccine production. Further, catalytic subunit analogs provide biological activity that is reduced in, or essentially free of, ADP-ribosyltransferase catalytic activity. The present analogs used alone, or in combination with B oligomer of the toxin (whether derived from natural sources or by recombinant means), can provide products that are useful in a vaccine and greatly reduce the likelihood of side-effects generally accepted to be associated with the catalytic activity in the native toxin. The toxin analogs of the present invention can be formulated into vaccine compositions or used in combination with other immunogenic agents in a multi-component vaccine.

The individual cistronic elements, or portions thereof, encoding the A (SEQ ID NO: 1) and B (SEQ ID NO: 3) subunits of *V. cholerae* toxin were subcloned and directly expressed individually in a recombinant host cell system (i.e., *E. coli*). In the absence of a native signal peptide (substituted with a methionine to initiate translation), high levels of expression, in the range of 2% to 80% of total cell protein, were obtained. The fermentation of expressor cells resulted in mature species of rCTXA, rCTXA1 and rCTXB, as shown in FIG. 3. It should be noted that rCTXA is not processed to rCTXA1 and rCTXA2 in *E. coli*, presumably due to the absence of the specific enzyme or a failure of rCTXA to be compartmentalized with this enzyme. Thus, rCTXA possesses the A1 sequence covalently linked to the A2 sequence.

Amino acid analysis of selected recombinant molecules demonstrated that the heterologous (non-native) methionyl residue is not substantially removed from the various rCTX and rCTXA1 subunit species by cellular methionine aminopeptidase; thus, these are also methionyl-mature analogs. All of the recombinant proteins were recovered as inclusion bodies from lysed cells. The subunits were found to have migration patterns in reducing SDS-PAGE essentially identical to authentic native subunits, with the exception of rCTXA which is not processed in *E. coli* to result in cleavage of the A2 region from A1. As shown in FIG. 3, high-level recombinant expression of subunits CTXA, CTXA1 and CTXB in *E. coli* was achieved by direct, non-fusion means.

Although alternative methods and materials can be used in the practice of the present invention, the preferred methods and materials are described below. All references cited hereunder are incorporated herein by reference.

MATERIALS AND METHODS FOR RECOMBINANT EXPRESSION OF CTXA, CTXA1 AND CTXB SUBUNITS

Materials. DNA modifying enzymes were purchased from New England Biolabs (Beverly, Mass.), Bethesda Research Laboratories (Gaithersburg, Md.), Boehringer Mannheim Biochemicals, (Indianapolis, Ind.), and International Biotechnologies, Inc. (New Haven, Conn.); enzymes were used according to manufacturer recommendations. All chemicals and biochemicals were analytical reagent grade. Purified, naturally-occurring cholera toxin and toxin subunits were purchased from Sigma Chemical Company (St. Louis, Mo.) and List Biologicals (Campbell, Calif.). Synthetic oligonucleotides were synthesized based on methods developed from the chemical procedure of Matteucci and Caruthers(18).

Plasmids and Bacterial Strains. Plasmids pRIT10810 and pRIT10841, (ATCC 39051 and ATCC 39053, respectively), containing the portions of the CTX operon, were obtained from the American Type Culture Collection, Rockville, Md. Expression plasmids pCFM1036, pCFM1146 and pCFM1156 were derived at Amgen.

A description of the expression vector system used herein is described in U.S. Pat. No. 4,710,473 (Morris), which is incorporated herein by reference. Such plasmids contain an inducible promoter, a synthetic ribosome binding site, a cloning cluster, plasmid origin of replication, a transcription terminator, genes for regulating plasmid copy number, and a Kanamycin resistance gene. The derived plasmids differ from each other in a number of respects. The plasmid pCFM1036 can be derived from pCFM836 (see U.S. Pat. No. 4,710,473) by substituting the DNA sequence between the unique AstII and EcoRI restriction sites containing the synthetic $P_L$ promoter with the following synthetic, double stranded linker fragment comprised of annealed oligonucleotides encoding the DNA sequences set forth in SEQ ID NO: 5 and SEQ ID NO: 6:

```
           AatII                         EcoRI

5'- CATCGATTCTAG-3'
         3'-TGCAGTAGCTAAGATCTTAA-5'
```

This plasmid contains no inducible promoter preceding the restriction cluster. The plasmid pCFM1146 can be derived from pCFM836 by substituting the small DNA sequence between the unique ClaI and XbaI restriction sites with the following synthetic, double stranded linker fragment comprised of annealed oligonucleotides encoding the DNA sequences set forth in SEQ ID NO: 7 and SEQ ID NO: 8:

```
           ClaI                 XbaI

5'-CGATTTGATT-3'
             3'-TAAACTAAGATC-5'
``` and by destroying the two endogenous NdeI restriction sites by end-filling with T4 polymerase enzyme followed by blunt-end ligation. The plasmid contains no synthetic ribosome binding site immediately preceding the restriction cluster. The plasmid pCFM1156 can be derived from pCFM1146 by substitution of the small DNA sequence between the unique XbaI and KpnI restriction sites with the following synthetic, double stranded DNA linker fragment comprised of annealed oligonucleotides encoding the DNA sequences set forth in SEQ ID NO: 9 and SEQ ID NO: 10. This fragment which installs an optimized synthetic ribosome binding site:

```
           XbaI                                            KpnI

5'-CTAGAAGGAAGGAATAACATATGGTTAACGCGTTGGAATTCGGTAC-3'
             3'-TTCCTTCCTTATTGTATACCAATTGCGCAACCTTAAGC-5'
```

Plasmids pBR322, pUC18, pUC19, and phage M13mp18 and M13mp19 DNA were purchased from Bethesda Research Laboratories. *E. coli* FM5 cells were derived at Amgen Inc., Thousand Oaks, Calif. from *E. coli* K-12 strain(19) from C. F. Morris and contain the integrated lambda phage repressor gene, $CI_{857}$(20). Construction of the individual subunit expression plasmids is described herein. Vector production, cell transformation, and colony selection were performed by standard methods(21).

Analytical Procedures. DNA sequencing was done by modification of the primer-extension, chain-termination method(22,23). Protein sequence analyses were performed by automated Edman degradation in an ABI 470A gas-phase microsequenator(24,25) and by standard enzymatic means, the latter to obtain carboxyl-terminal sequences of selected-proteins. SDS-polyacrylamide gel electrophoresis (SDS-PAGE) was performed essentially as described by Laemmli (26), and elution of polypeptides from polyacrylamide gels was similar to the method of Hunkapiller et al.(27). The ratio of recombinant protein to total cellular protein or total inclusion body protein was assessed by SDS-PAGE of whole-cell lysates followed by staining with Coomassie Brilliant Blue R250 and subsequent gel scanning by integrative densitometry.

Assays for the measurement of ADP-ribosyltransferase catalytic activity were done as follows: Native CTXA and recombinant subunits were incubated in a solubilization buffer of 8M urea, 25 mM sodium phosphate (pH 7.0) and 10 mM dithiothreitol (DTT) for one hour at 37° C. and centrifuged at 10,000 rpm for 15 minutes without refrigeration. The additions to the solubilization buffer were adjusted to yield 1 μg of native or recombinant A1 per 4 μL, which was then added to 60 μL of a reaction mixture (see below) and incubated for one hour on ice.

| Reaction Mixture | | |
|---|---|---|
| Reagent*: | (final)/60 μl | (final)/100 μl |
| $Na_xPO_4$, pH 7.0, 1 M | 416 mM | 250 mM |
| DTT, 100 mM | 5 mM | 3 mM |
| GTP, 10 mM | 167 μM | 100 μM |
| Thymidine, 100 mM | 17 mM | 10 mM |
| $MgCl_2$, 1 M | 5 mM | 3 mM |
| [32p]-NAD | 2.5 μCi | 2.5 μCi |
| AND, 2500 μM | 50 μM | 30 μM |

*The reagents were obtained from commercial sources. Naturally-occurring CTXA was acquired from List Laboratories. As a control, native CTXA was also assayed by incubation in the same buffer as above, but without urea, for 15 minutes at 37° C., then kept on ice until assayed for ADP-ribosyltransferase activity.

Thirty-six μL of water or a buffer containing human erythrocyte membranes(28) were added to yield a final volume of 100 μL for each sample and the samples incubated at 30° C. After 30 minutes, the reaction was terminated by adding 50 μL of 5 mM NAD and 0.03% sodium deoxycholate to each sample and the reaction mixture chilled on ice for 10 minutes. Fifty μL of 40% trichloroacetic acid (TCA) were then added, the samples placed on ice for at least 15 minutes; 2 mL of water were subsequently added to each sample, and the precipitated protein pelleted by centrifugation. The supernatants were removed and the pelleted protein was frozen. On the following day, the pelleted protein was subjected to SDS-PAGE(26,29). The gel was stained with Coomassie Brilliant Blue, destained, dried and subjected to autoradiography to measure the content of covalently linked [$^{32}$P]-labeled ADP-ribose in the proteins of the various bands. An approximation of the specific activities of the recombinant CTXA1 and recombinant analog CTXA1 proteins (relative to the activity of native CTXA1) was obtained by densitometric scanning of the gels and autoradiograms. The stained gels were scanned to approximate the amount of individual protein added to each reaction mixture. The autoradiograms were scanned to estimate the amount of [$^{32}$P]ADP-ribose transferred to the G protein substrate as a function of the density of the autoradiographic image.

Construction of Expression Plasmids. All expression plasmids were constructed from a series of *E. coli* generalized expression vectors differing as described previously. The individual cholera toxin subunit gene segments were isolated using the restriction sites shown in FIGS. 1 and 2. The upstream restriction site was just inside the codon for the amino-terminal residue of the mature, processed form of the subunit (i.e., without the signal sequence). For purposes of recombinant expression in *E. coli,* the portion of the CTX genes encoding their native signal peptides were deleted and substituted instead by a methionine initiation codon, for expression of the "methionyl-mature" form of the subunit analogs. Synthetic oligonucleotide linkers were employed to effect insertion of the gene segments into the expression plasmids at an optimal distance downstream of the synthetic promoter and ribosome binding site. The upstream linkers restored the reading frame of each gene back to the first codon of the mature amino terminus; the oligonucleotides included a methionyl initiation codon.

Following transformation of *E. coli* FM5 cells with the various plasmid constructs and plating on Kanamycin-containing agar, appropriate numbers of colonies were selected, replica-plated, grown as small liquid cultures ("minipreps"), and induced at 42° C. for 4 hours. The minipreps were then screened by light microscopy for the presence of inclusion bodies in the bacterial cells. Preparations exhibiting apparent inclusion bodies were identified and matching colonies from the replica plates subjected to flask-scale laboratory fermentation at the induction temperature. Samples were removed from fermentation at various times post-induction and examined for the appearance of the appropriate CTX subunit by SDS-PAGE followed by Coomassie Brilliant Blue-staining. The structure of the plasmid from each expression clone was confirmed by restriction mapping of the isolated plasmid and verified by DNA sequencing of junction regions.

Expression of Recombinant CTX, CTXA1 and CTXB. When *E. coli* cells containing, separately, the CTXA expression plasmid (pCTXA/A7/1156), the CTXA1 expression plasmid (pCTXA1/A7/1156), and the pCTXB expression plasmid (pCTXB/1156) were fermented at 37° C. and 42° C., they produced major intracellular proteins (FIG. 3) of approximately 27,215 daltons, 21,817 daltons and 11,600 daltons, respectively; recombinant CTXA1 and CTXB comigrated with authentic (native) CTXA1 and CTXB, respectively, in SDS-PAGE. Our recombinant CTXA has no native counterpart, since natural CTXA is cleaved to CTXA1 and CTXA2 by *V. cholerae* protease at some point before secretion from the organism; A1 and A2 are held together by a disulfide bond that is reduced by the buffers used in SDS-PAGE. Partial amino acid sequence analysis established that recombinant polypeptide CTXA1/A7 and CTXA1/L7 (see description below) had the amino terminal sequence predicted for the native CTXA1 subunit, but that the heterologous initiating methionine residue is not substantially removed.

Properties of Recombinant CTX Subunits. Very little, if any, of the CTX subunits appear to be secreted from the *E. coli* cells. The bulk of each subunit was found in the form of inclusion bodies and constituted 2% to 80% of total cellular protein. Cell lysis by French press and low speed centrifugation resulted in pellet fractions that contained up to 80% of their protein as the individual subunits. All the rCTX subunits were detectable in gels stained with Coomassie Brilliant Blue (FIG. 3).

CTXA AND CTXA ANALOGS

Using techniques of protein engineering and site-specific mutagenesis(19,30), CTXA and CTXA1 analogs were made. From those analogs made and tested by the time of this submission, it was found that mutagenesis of the amino acid residues at positions arginine-7, histidine-44, histidine-70, glutamic acid-112, and aspartic acid-9, and truncation of the carboxyl terminus (at tryptophan-179 of the mature native CTXA sequence) resulted in diminished or essentially no ADP-ribosyltransferase activity.

Construction of the CTXA Expression Plasmid. Plasmid pRIT10841 (ATCC 39053) was cleaved with restriction enzymes XbaI and ClaI and a 552-bp DNA fragment was isolated by gel electrophoresis which contained the left-hand end of the CTXA gene to the region encoding the protease-sensitive portion that results in CTXA cleavage to CTXAl and CTXA2. Plasmid pRIT10810 (ATCC 39051) was cleaved with restriction enzymes ClaI and HindII (the latter an isoschizomer of HincII) and a 368-bp DNA fragment was isolated that encoded a portion of the CTXA subunit from the protease-sensitive site (encoded at the ClaI site) (16,17) through the CTXA2 region, past the termination codon of CTXA, and into the alternative open reading frame of the CTXB subunit.

A synthetic double stranded oligonucleotide linker (comprised of DNA molecules encoding the DNA sequences set forth in SEQ ID NO: 11 and SEQ ID NO: 12) was prepared to reconstitute the open reading frame of CTXA from the site encoding the first amino acid of the mature protein sequence (asparagine) to the XbaI site. This linker possessed NdeI cohesiveness at its left-hand end in order to generate a methionine initiation codon that would substitute for the sequence encoding the signal peptide and to facilitate insertion of the gene construction into the expression vector; the right-hand end of the linker possessed an XbaI overlap. This linker possessed the sequence:

5'-TATGAATGATGATAAGTTATATCGGGCAGATT-3'3'-ACT-
TACTACTATTCAATATAGCCCGTCTAAGATC-5'

Plasmid pUC19 was digested with NdeI and XbaI and the linker above inserted. After ligation and transformation, a pUC plasmid named p2A/pUC19 was isolated that contained the linker sequence in place of the normal pUC19 NdeI-XbaI sequence.

Plasmid p2A/pUC19 was digested with XbaI and HincII. The large fragment from this digestion was ligated together with the 552-bp XbaI-ClaI DNA fragment containing the left-hand end of the CTXA gene and the 368-bp ClaI-HindII DNA fragment containing the right-hand end of the CTXA gene (past the termination codon and into the alternative open reading frame of the CTXB subunit). This produced a new plasmid containing the entire mature CTXA gene; this plasmid was called pCTXA/A7/pUC19.

The *E. coli* expression plasmid pCFM1156 was digested with NdeI and HindIII to remove this small portion of its cloning cluster. Plasmid pCTXA/A7/pUC19 was also digested with NdeI and HindIII, and a DNA fragment (772-bp) containing the entire region of the CTXA gene was isolated. This fragment was subsequently ligated into the digested pCFM1156 plasmid to produce the CTXA expression plasmid pCTXA/A7/1156. This NdeI-NdeI fragment could be inserted into pCFM1156 in either of two orientations, only one of which would produce an open reading frame giving rise to a large protein when expressed. This clone was selected (by analysis of induced clones by SDS-PAGE to identify the recombinant CTXA protein) and the proper orientation confirmed by DNA sequencing at the upstream NdeI junction region.

Construction of the CTXB Expression Plasmid. Plasmid pRIT10810 (ATCC 39051) was digested with ClaI and BstXI and a 538-bp DNA fragment was isolated; this contained the the A2 coding region of CTXA, the entire CTXB coding region, and a short DNA sequence to the right of the termination codon of CTXB.

A synthetic, double stranded oligonucleotide linker (comprised of annealed, single stranded oligonucleotides encoding the DNA sequences set forth in SEQ ID NO: 13 and SEQ ID NO: 14) was prepared that permitted the cloning of the right-hand end of the DNA sequence above into pUC19. This linker possessed BstX1 and HindIII cohesive ends and had the sequence:

5'-GTGGAATTCGGTACCATGGA-3'3'-GAGTCACCTTAAGC-
CATGGTACCTTCGAA-5'

Plasmid pUC19 was digested with HindIII and AccI (the latter generating a cohesive end compatible with that generated by ClaI). The large pUC19 fragment was ligated with the 538-bp ClaI-BstXI DNA fragment containing the CTXB and the BstXI-HindIII linker to produce a plasmid called pCTXB/pUC19. This plasmid was then digested with HindIII and SspI (the latter just inside the initiation codon for CTXB and downstream from the ClaI site) to isolate a 345-bP SspI-HindIII fragment.

A synthetic double stranded oligonucleotide linker (comprised of annealed, single stranded oligonucleotides encoding the DNA sequences set forth in SEQ ID NO: 15 and SEQ ID NO: 16) was prepared that possessed NdeI and SspI cohesive ends and the sequence:

5'-TATGACACCTCAAAAT-3'3'-ACTGTGGAGTTTTA-5'

Plasmid pCFM1156 was digested with NdeI and HindIII to remove this portion of its cloning cluster. The large pCFM1156 DNA fragment was then ligated with the 345-bp SspI-HindIII fragment containing a portion of the CTXB gene and the NdeI-SspI linker that restored its left-hand coding region and insinuated a methionine codon at the left of this coding region to initiate protein synthesis. The subsequent expression plasmid, containing the entire CTXB gene with a methionine initiation codon, was called pCTXB/1156.

Linker Mutagenesis. A synthetic, double stranded oligonucleotide linker (comprised of annealed, single stranded oligonucleotides encoding the DNA sequences set forth in SEQ ID NO: 17 and SEQ ID NO: 18) called L7 was synthesized to substitute a lysine codon for that of arginine-7 in CTXA. The sequence of this linker, with NdeI and XbaI cohesive ends, is shown in Table 1. The L7 linker was cloned into the NdeI-XbaI site of pUC19 to produce a plasmid called pL7/pUC19. Plasmid pL7/pUCl9 was then digested with XbaI and HindIII to remove this portion of the pUC19 cloning cluster and replaced through ligation with the 552-bp XbaI-ClaI DNA fragment containing the left-hand end of the CTXA gene (see above) and the 368-bp ClaI-HindII DNA fragment containing the right-hand end of this gene (see above). This plasmid, called pCTXA/L7/pUC19, was digested with NdeI, and a 772-bp DNA fragment was isolated that possessed the entire mature CTXA gene with a substitution of the arginine-7 codon by a lysine codon. Plasmid pCFM1156 was digested with NdeI and ligated with the NdeI DNA fragment from pCTXA/L$^7$/pUC19. This ligation produced a plasmid called pCTXA/L$^7$/1156 for expression of the mature form of an Arg$^7$→Lys analog of CTXA in E. coli. As with the case of pCTXA/A7/1156 (above), it was necessary to select a clone containing this plasmid with the DNA insert in the proper open reading frame for synthesis of rCTXA/L7.

Synthetic double stranded oligonucleotide linkers IE (comprised of annealed, single stranded oligonucleotides encoding the DNA sequences set forth in SEQ ID NO: 19 and SEQ ID NO: 20) and 1F (comprised of annealed, single stranded oligonucleotides encoding the DNA sequences set forth in SEQ ID NO: 21 and SEQ ID NO: 22) synthesized to individually substitute, respectively, a phenylalanine codon for that of tyrosine-6 and a glutamate codon for that of aspartate-9. These linkers possessed NdeI and XbaI cohesive ends and had the sequences shown in Table 1. Plasmid pCTXA/A7/pUC19 (see above) was digested with XbaI and HindIII, and a 938-bp DNA fragment containing the right-hand portion of the CTXA gene was isolated. Plasmid pCFM1156 was digested with NdeI and HindIII to remove this short region of its cloning cluster. This segment was replaced by ligation with the NdeI-XbaI linker containing either the Tyr$^6$→Phe or the Asp$^9$→codon mutation (linkers 1E and 1F, respectively) and the 938-bp DNA fragment of the CTXA gene. This produced two plasmids, pCTXA/1E/1156 and pCTXA/1F/1156, for expression of the mature forms of the CTXA analogs Tyr$^6$→Phe and Asp9→Glu, respectively, in E. coli.

The substitutions of sequences encoding mutations of glutamine for proline-185 and alanine for cysteine-18$^7$ resulted in CTXA gene fragments encoding only the CTXA1 portion of the CTXA subunit (see below for construction of the native-sequence CTXA1 gene and the L7, 1E, and 1F substitution analogs of CTXA1 from the CTXA gene and its substitution analogs, respectively). Oligonucleotide linkers 1G (comprised of annealed, single stranded oligonucleotides encoding the DNA sequences set forth in SEQ ID NO: 23 and SEQ ID NO: 24) and 1H comprised of annealed, single stranded oilgonucleotides encoding the DNA sequences set forth in SEQ ID NO: 25 and SEQ ID NO: 26) were synthesized to individually substitute, respectively, glutamine for proline-185 and alanine for cysteine-187. These linkers had DsaI and HindIII cohesive ends and possessed the sequences shown in Table 1. To effect the construction of the expression plasmids encoding the analog proteins, a 537-bp NdeI-DsaI DNA fragment was isolated from plasmid pCTXA/A7/pUC19. Plasmid pCFM1156 was then digested with NdeI and HindIII to remove this short segment of its cloning cluster. This segment was replaced by ligation with the 537-bp DNA fragment from pCTXA/A7/pUC19 and either 1G or 1H synthetic oligonucleotides. The linkers, in addition to encoding the specific amino acid substitutions, eliminate from the CTXA gene that portion encoding the A2 region of the CTXA subunit; thus, these mutations are exclusively in CTXAl versions of the subunit. The resulting plasmids for expression of the Pro$^{185}$→Gln and Cys$^{187}$→Ala analogs of CTXA1 were called pCTXA1/1G/1156 and pCTXA1/1H/1156, respectively.

A plasmid expressing a carboxyl-terminal truncated version of CTXA1 terminating at Trp$^{179}$ was constructed. This was accomplished by first digesting plasmid pCFM1156 with NdeI and HindIII to remove this short DNA fragment. Into this site in pCFM1156 was ligated the 537-bp NdeI-DsaI fragment from pCTXA/A7/PUC19 (see above) and a synthetic DNA fragment (comprised of annealed, single stranded oligonucleotides encoding the DNA sequences set forth in SEQ ID NO: 27 and SEQ ID NO: 28) with DsaI and HindIII cohesive ends, and having the sequence:

5'-CGTGGTAATGATAGA-3'3'-CATTACTATCTTCGA-5'

This plasmid, for expression of CTXA1 truncated at Trp$^{179}$, was called pCTXA1/T1/1156.

Mutagenesis By Site-directed Priming

Mutagenesis by site-directed priming was accomplished with kits of the "Altered Sites™ in vitro Mutagenesis System" purchased from Promega Corporation (Madison, Wis.); details of the experimental protocols for this procedure are contained in the technical manual available from Promega Corporation (printed 1/90).

To facilitate mutagenesis, a 938-bp XbaI-HindIII DNA fragment encoding a portion of the CTXA subunit was isolated from plasmid pCTXA/A7/pUC19 (see above). This fragment was cloned into the pSELECT1 phagemid vector from-Promega. After packaging with helper phage, this vector contained a negative-sense copy of the CTXA fragment. A series of single-stranded, positive-sense DNA primers were synthesized to effect mutagenesis; the sequences of these primers (1B (SEQ ID NO: 29), 1C (SEQ ID NO: 30), 1D (SEQ ID NO: 31), and 1I (SEQ ID NO: 32)) are shown in Table 1. These primers were individually annealed with the single-stranded phagemid containing the CTXA gene fragment; double-stranded phagemids were subsequently produced which contained the gene fragment and the individual codon substitutions encoded by the primers.

For preparation of plasmids capable of expressing the CTXA and CTXA1 subunit analogs containing a lysine substitution for arginine-146, a 207-bp BstXI-ClaI DNA fragment was isolated from the double-stranded phagemid containing the Arg$^{146}$→Lys codon mutation (1I). A 375-bp NdeI-BstXI DNA fragment and a 386-bp ClaI-HindIII fragment (for the CTXA version) containing a portion of the CTXA gene were isolated from plasmid pCTXA/A7/pUC19. Plasmid pCFM1156 was digested with NdeI and HindIII to remove this short portion of its cloning cluster. For construction of the CTXA version of the Arg$^{146}$→Lys mutation, the digested pCFM1156 plasmid was ligated with the 375-bp NdeI-BstXI fragment from pCTXA/A7/pUC19, the 209-bp BstXI-ClaI fragment from the double-stranded phagemid, and the 386-bp ClaI-HindIII DNA fragment from pCTXA/A7/pUC19. This resulted in a plasmid called pCTXA/1I/1156 for expression of the Arg146→Lys analog of the CTXA subunit in E. coli. For construction of this mutation in the CTXA1 version of the subunit, the digested pCFM1156 plasmid was ligated with the 375-bp NdeI-BstXI fragment from pCTXA/A7/pUC19, the 209-bp BstXI-ClaI fragment isolated from the double-stranded phagemid, and a synthetic double stranded oligonucleotide linker (comprised of annealed, single stranded oligonucleotides encoding the DNA sequences set forth in SEQ ID NO: 33 and SEQ ID NO: 34) that replaces a region of CTXA encoding the A2 portion of CTXA with a DNA sequence encoding the end of the Al region and including a codon that terminates polypeptide synthesis at the end of CTXA1. This linker possessed ClaI and HindIII cohesive ends and had the sequence:

5'CGTAATAGGCGGCCGCA-3'3'-ATTATCCGCCGGCGTCGA-5'

The resultant plasmid for expression of the Arg$^{146}$→Lys analog of CTXAl in E. coli was called pCTXA1/1I/1156.

Preparation of plasmids capable of expressing individual analogs of CTXA containing the substitutions of His$^{44}$→Asn, His$^{70}$→Asn, or Glu$^{112}$→Gln was facilitated with primers (1B, 1C, and 1D, respectively) having the sequences shown in Table 1. After annealing of the primers individually to the pSELECT1 phagemid containing the 938-bp XbaI-HindIII CTXA fragment from pCTXA/A7/pUC19 (see above) and recovering double-stranded plasmid, the regions containing the site-specific mutations were excised from the plasmid by digesting with XbaI and HindIII, and recovering a 938-bp DNA fragment in each case. Plasmid p2A/pUC19 (containing an NdeI-XbaI linker encoding the left-hand end of the mature CTXA; see above) was digested with XbaI and HindIII to remove this short region of the pUC19 cloning cluster to the right of the linker insert; this region was replaced by ligation with the 938-bp XbaI-HindIII fragment from the plasmid containing a single codon replacement. This series of pUC-derived plasmids were called pCTXA/1B/pUC19, pCTXA/1C/pUC19, and pCTXA/1D/pUC19, depending upon the codon replacement they contained. A DNA fragment containing the codon replacement was subsequently excised from each of these plasmids. Plasmid CTXA/A7/pUC19 was digested with BstXI and HindIII and a 593-bp DNA fragment was isolated. Plasmid pCFM1156 was digested with NdeI and HindIII to remove this short region of its cloning cluster,-as described earlier, and this replaced by ligation with the individual CTXA analog gene inserts recovered from the pUC transition plasmids above and the 593-bp BstXI-HindIII DNA fragment from pCTX/A7/pUC19. When isolated, these new plasmids for expression of the site-specific analogs His$^{44}$→Asn, His$^{70}$→Asn, and Glu$^{112}$→Gln of CTXA in E. coli were called pCTXA/1B/1156, pCTXA/1C/1156, and pCTXA/1D/1156, respectively.

Conversion of CTXA and CTXA Analog Genes to CTXA1 and CTXA1 Analoa Genes. With the exception of the plasmid containing the 1I codon substitution (pCTXA1/1I/1156), which was constructed during the mutagenesis process to lack the A2-encoding region, it was useful to convert the CTXA gene-containing and selected individual analog gene-containing expression plasmids to CTXA1 expression plasmids in order to express the A1 truncated version of CTXA that mimicked the native species of this subunit in reduced holotoxin preparations. To perform this conversion, it was necessary to delete a portion of the gene sequence of the CTXA gene (and the analog genes) to the right of the unique ClaI site. Although the actual site of polypeptide cleavage between the A1 and A2 regions has not been resolved in the prior art literature(16,17), it was decided to initially establish the carboxyl terminus of A1 at serine-194; it should be noted, however, that establishing the terminus at arginine-192 (the other terminus proposed in the literature) is a simple matter of inserting a new linker to substitute a termination codon immediately to the right of the arginine-192 codon.

For our purposes, each of the analog CTXA sequences (and the native CTXA sequence) we wished to convert to CTXAl versions were excised from their pUC19 transition plasmids (i.e., pCTXA/A7/pUCl9, pCTXA/1B/pUC19, pCTXA/1C/pUC19, pCTXA/1D/pUC19, pCTXA/1E/pUC19, pCTXA/1F/pUC19, pCTXA/1G/pUC19, pCTXA/1H/pUC19) with restriction enzymes NdeI (at the sequence encoding the methionine initiation codon) and ClaI (at the site chosen for addition of a termination codon immediately to the right of the serine-194 codon); this DNA fragment was 585-bp in each case. For purposes of substituting a termination codon for the A2-encoding region and subsequent ligation of the gene segments into plasmid pCFM1156, an oligonucleotide linker was synthesized to possess ClaI and HindIII cohesive ends and had the following sequence:

5'-CGTAATAGGCGGCCGCA-3'3'-ATTATCCGCCGGCGT-
TCGA-5'

Plasmid pCFM1156 was digested with NdeI and HindIII to remove this portion of its cloning cluster; this region was replaced by ligation with the ClaI-HindIII linker and with an individual 585-bp DNA fragment from one of the pUC transition plasmids described above. Isolation of plasmid DNA following these ligations resulted in a series of plasmids capable of expressing CTXA1 and CTXA1 analog polypeptides in E. coli; plasmids prepared in this manner included pCTXA1/1B/1156, pCTXA1/1C/1156, pCTXA1/1D/1156, pCTXA1/1E/1156, and pCTXA1/1F/1156.

Figure 4A:
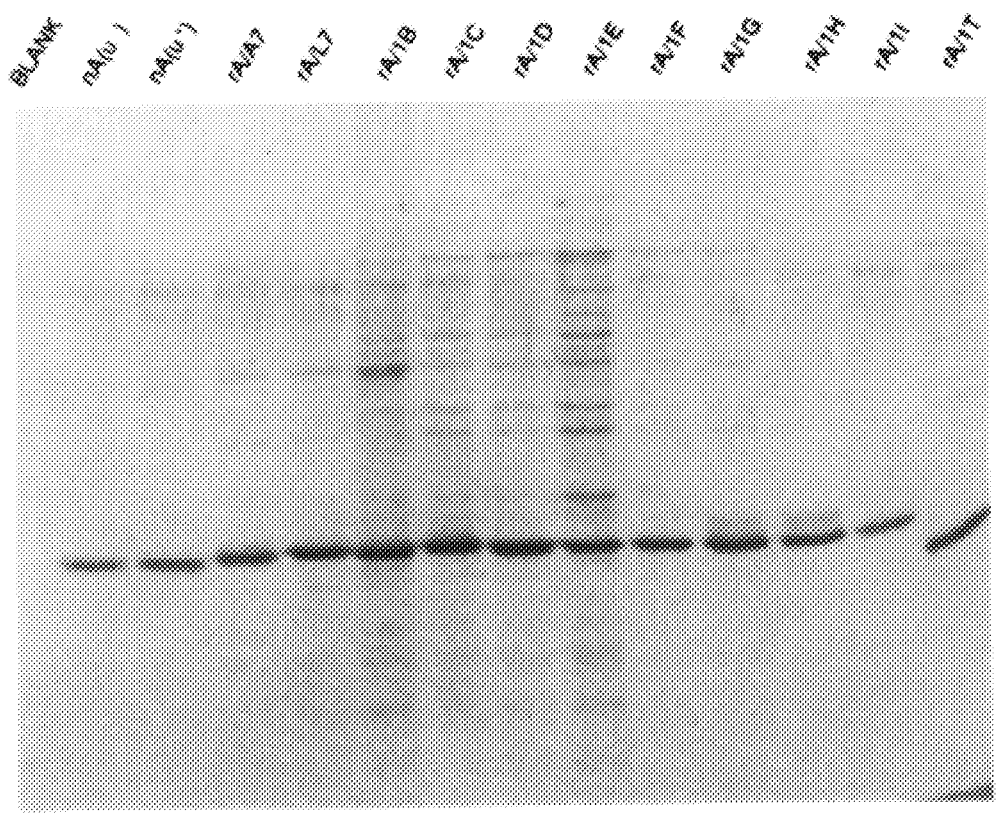
FIGS. 4A–4C are the SDS-PAGE and autoradiographic analysis of rCTXA1 and CTXA1 analog ADP-ribosyltransferase activity. In Panel A, native CTXA, recombinant CTXA1, and various site-specific analogs or preparations of rCTXA1 were subjected to SDS-PAGE and stained with Coomassie Blue. These same preparations were used as enzyme sources to ADP-ribosylate membrane-associated G protein using [$^{32}$P]NAD under assay conditions described in the text. After the reactions were quenched, the entire reaction mixture from each preparation was subjected to SDS-PAGE, and the gel dried and subjected to autoradiography to visualize proteins that have been covalently modified by addition of [$^{32}$P]-labeled ADP-ribose. Panel 4B shows the result of the assays when no G-protein substrate was added, illustrating the ability of recombinant CTXA1 to autoribosylate; interestingly, analog CTXA1/L7 has lost this reactivity. Panel 4C shows the ADP-ribosylation of substrate G protein found in human erythrocyte membranes. Addition of this substrate substantially shifts reactivity of the enzyme from itself (autoribosylation) to the target G protein (seen in the autoradiogram as its ribosylated a-subunit). Again, rCTXAl analog L7 lacks this reactivity.
Figure 4B:
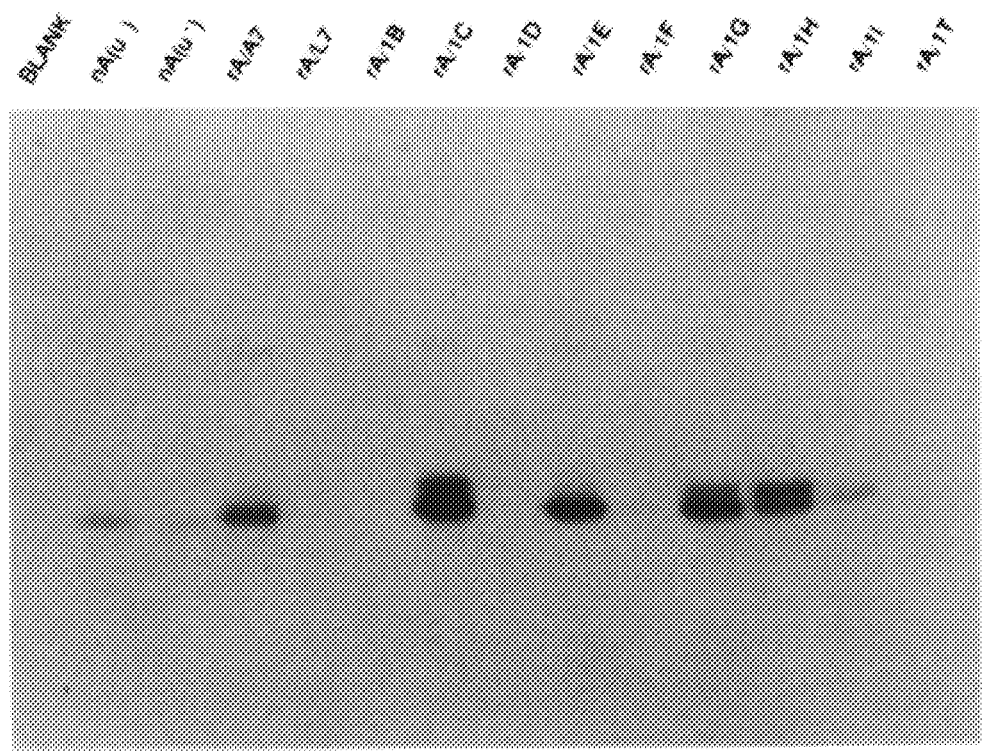
Figure 4C:
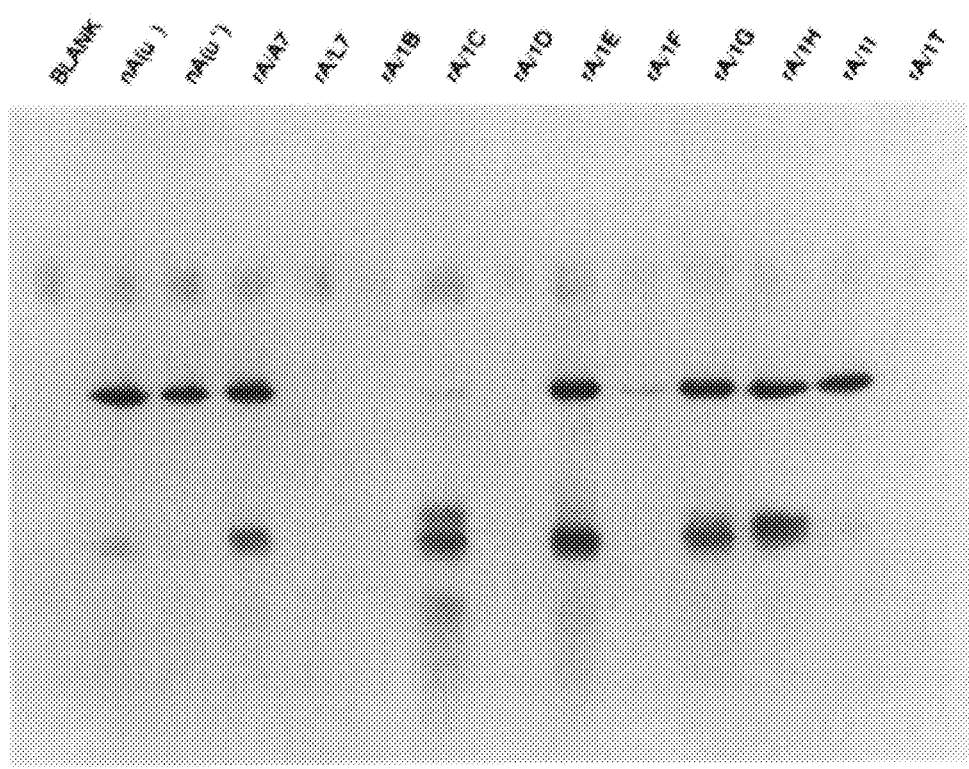
Figure 5A:
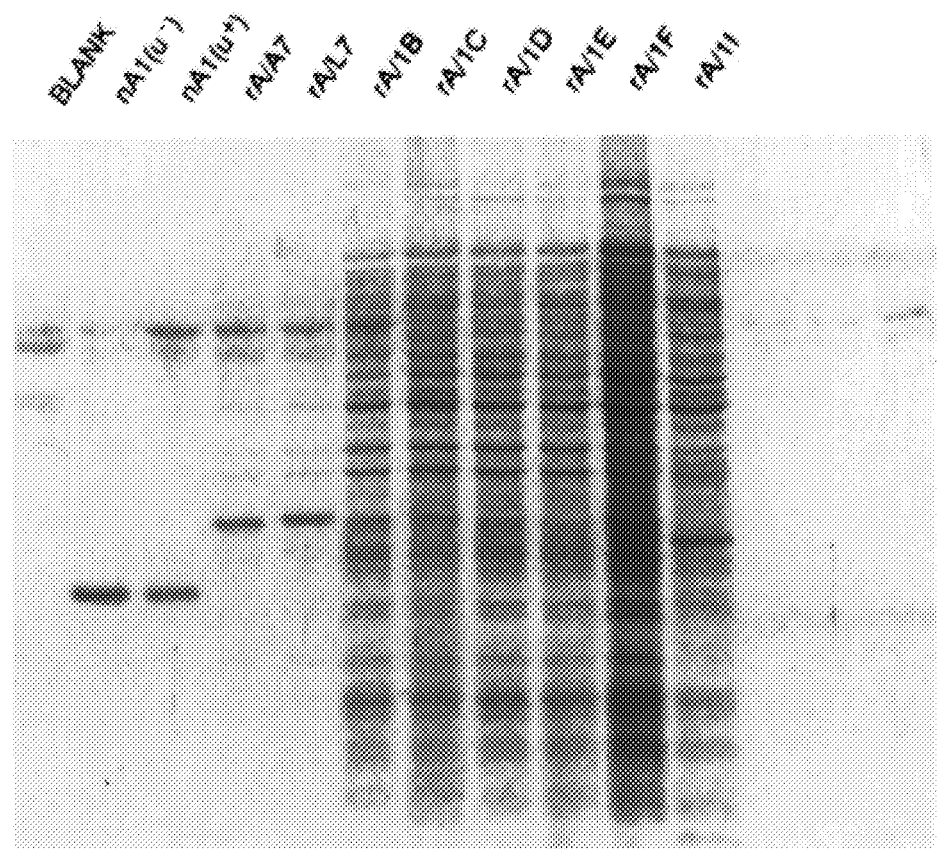
FIGS. 5A–5C are the SDS-PAGE and autoradiographic analysis of rCTXA and rCTXA analog ADP-ribosyltransferase activities, similar to that shown for rCTXA1 in FIGS. 4A–4C. Because the rCTXA preparation possesses significantly lower activity than rCTXA1 (see FIGS. 6A&6B), presumably because the former still contains the uncleaved A2 "tail" at its carboxyl terminus, these autoradiograms were attained by a longer exposure of the gel (Panel A) to the x-ray film. Panel 5A is the stained SDS-polyacrylamide gel of the rCTXA proteins; in comparison with FIG. 4, Panel A, it is evident that the recombinant expression of these proteins is generally less than that of the companion rCTXAl proteins. The Recombinant CTXA preparation was capable of autoribosylation (Panel 5B) and of ADP-ribosylating the G protein substrate in human erythrocyte membranes (Panel 5C); these activities are substantially diminished in comparison with rCTXAl. Nevertheless, the CTXA preparations exhibit the same general pattern of inactivation as do their CTXAl counterparts. Again, the L7 analog ($Arg7 \rightarrow Lys$) is devoid of ADP-ribosylating activity.
Figure 5B:
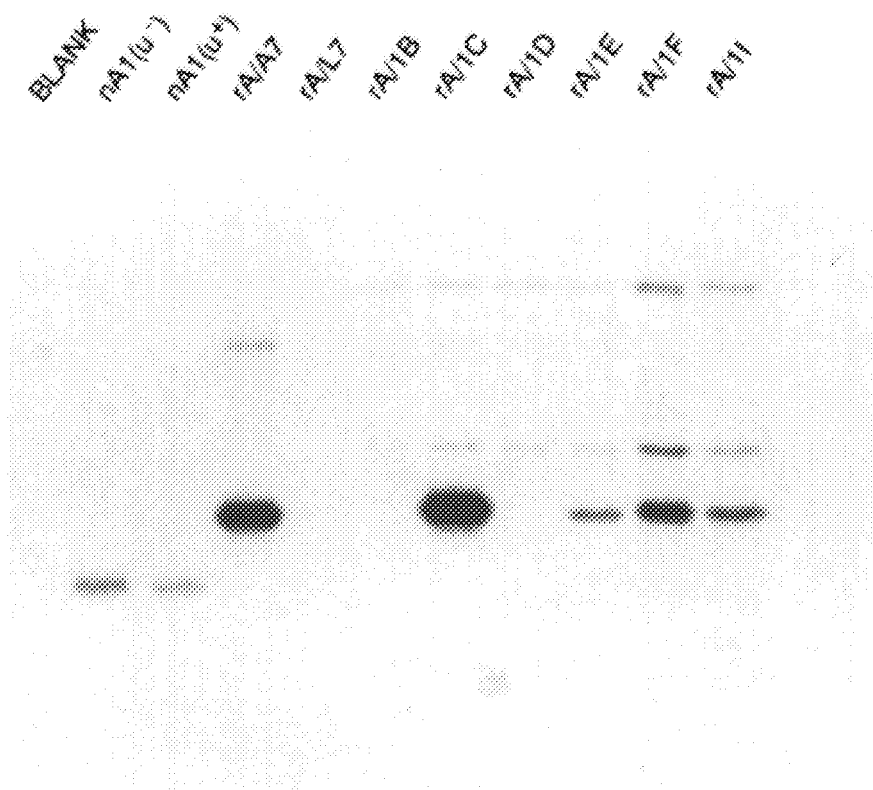
Figure 5C:
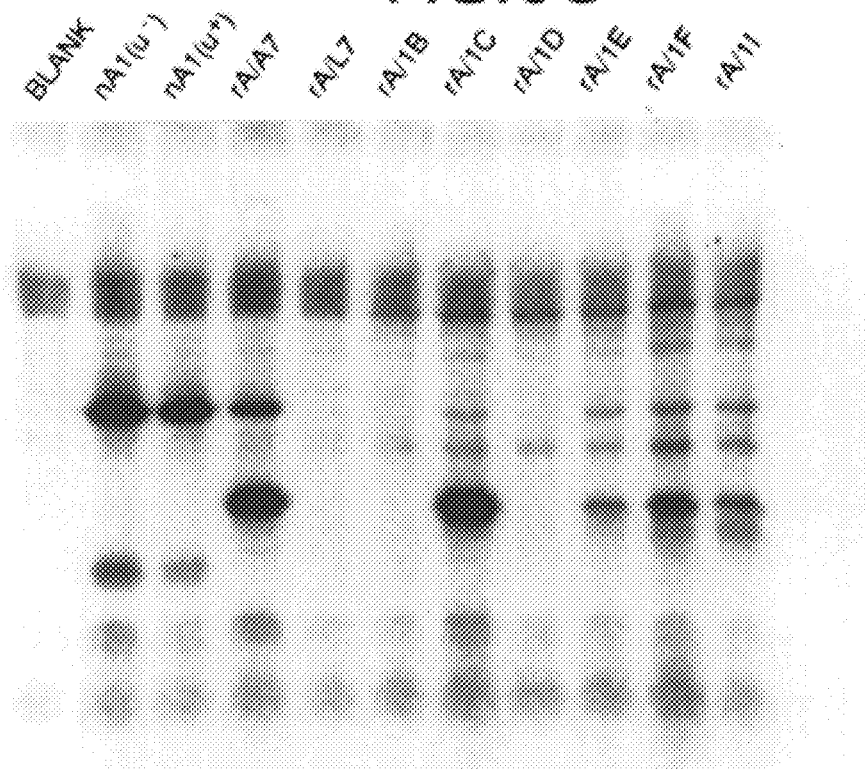
Figure 6A:
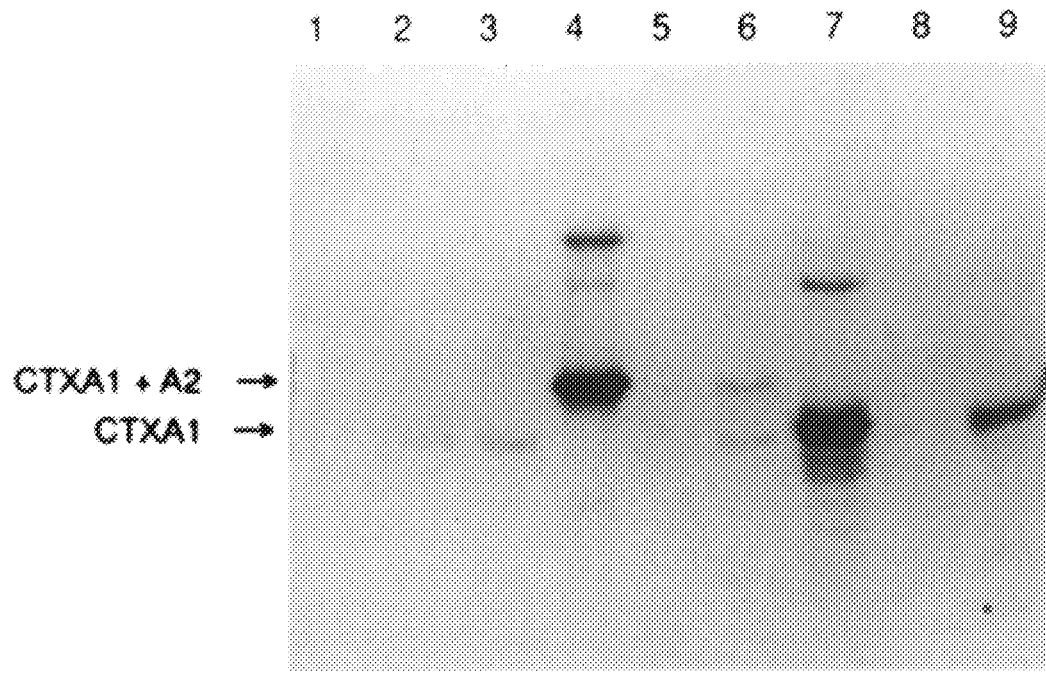
FIGS. 6A and 6B are the SDS-PAGE and autoradiographic comparison of the ADP-ribosyltransferase activity of rCTXA and rCTXA1/L7 with that of rCTXA1 and rCTXA1/L7. Panel 6A is the reactivity without added substrate and Panel 6B is with human erythrocyte membranes added as substrate. The lanes contain: lane 1) blank (no sample added to reaction); lane 2) native CTXA without urea treatment; lane 3) native CTXA with urea treatment; lane 4) rCTXA; lane 5) rCTXA/L7; lane 6) rCTXA/L7 plus native CTXA; lane 7) rCTXAl; lane 8) rCTXA/L7; lane 9) rCTXA1/L7 plus native CTXA. This experiment demonstrates that the rCTXA preparation is much less active than rCTXA1 for ADP-ribosylation of G proteins (compare lanes 4 and 7), yet exhibits substantial autoribosylating activity. Confirming the data shown in FIGS. 4(A–C) and 5(A–C), substitution of lysine for arginine-7 in rCTXA and rCTXA1 abolishes their ribosylating activities, both for autocatalysis and for G protein. Retention of activity by native CTXA when added to the analog preparations (lanes 6 and 9) additionally illustrates that it is not a contaminant of the recombinant preparations that suppress this activity.
Figure 6B:
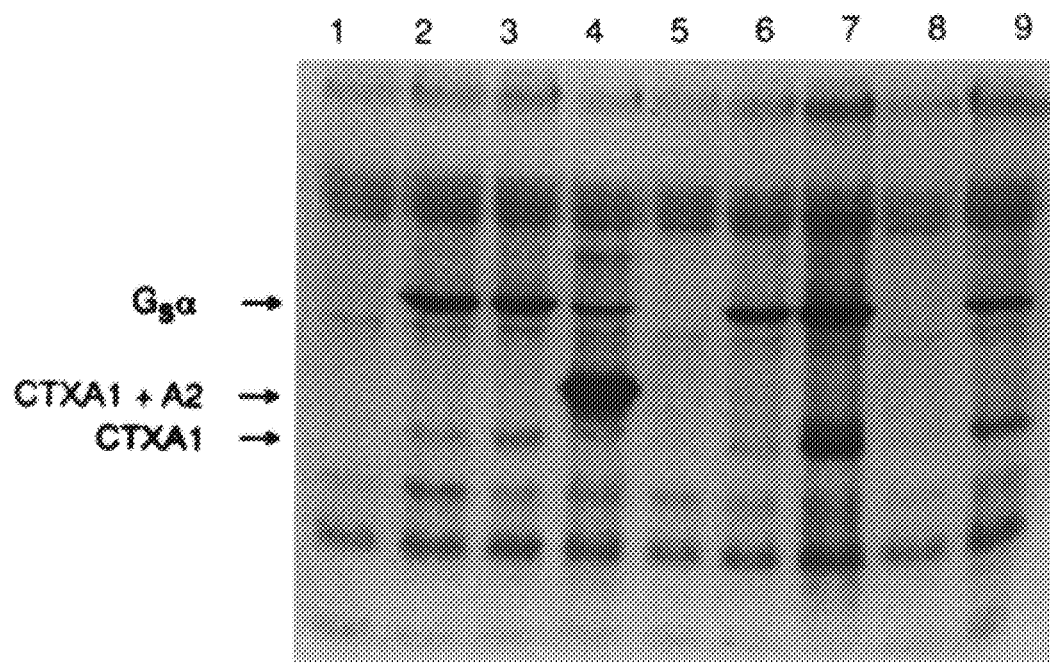

Expression and Analysis of CTXA and Recombinant Analogs. Following preparation, each plasmid was used to transform a separate preparation of fresh, competent FM5 cells. Transformants were picked, grown as minipreps, induced to produce recombinant protein, and inclusion body-positive samples identified by light microscopy. These samples were fermented at a larger scale ($\geq 1$ liter) at the induction temperature to prepare greater amounts of each recombinant analog protein. Isolated cell pastes were lysed in a French press after resuspension in distilled $H_2O$ with 1 mM DTT. Inclusion bodies were isolated from these lysates by simple low-speed centrifugation. These inclusion-body protein preparations contained as little as 2% and as much as 80% of the recombinant proteins. The samples were assessed for ADP-ribosyltransferase activity as previously described. The results obtained are shown in FIGS. 4, 5, and 6 and in Table 2.

TABLE 1

CONSTRUCTION OF S1 ANALOGS

| * | MUTATION | TECHNIQUE | OLIGONUCLEOTIDE SEQUENCE |
|---|---|---|---|
| L7 | ARG7->Lys | Linker Insertion | 5'-TATGAATGATGATAAGTTATATAAGGCAGATT-3'<br>3'-ACTTACTACTATTCAATATATTCCGTCTAAGATC-5' |
| 1B | His44->Asn | Site-directed Priming | 5'-CCTTTATGATAACGCAAGAGGAA-3' |
| 1C | His70->Asn | Site-directed Priming | 5'GAGAAGTGCCAACTTAGTGGGTC-3' |
| 1D | Glu112->Gln | Site-directed Priming | 5'-AGATGAACAACAGGTTTCTGCTT-3' |
| 1E | Tyr6->Phe | Linker Insertion | 5'-TATGAATGATGATAAGTTATTCCGGGCAGATT-3'<br>3'-ACTTACTACTATTCAATAAGGCCCGTCTAAGATC-5' |
| 1F | Asp9->Glu | Linker Insertion | 5'-TATGAATGATGATAAGTTATATCGGGCAGAAT-3'<br>3'-ACTTACTACTATTCAATATAGCCCGTCTTAGATC-5' |
| 1G | Pro185->Gln | Linker Insertion | 5'-CGTGGATTCATCATGCACCGCAGGGTTGTGGGAATGCTCCAAGATCATCGTAGA-3'<br>3'-CTAAGTAGTACGTGGCGTCCCAACACCCTTACGAGGTTCTAGTAGCATCTTCGA-5' |
| 1H | Cys187->Ala | Linker Insertion | 5'-CGTGGATTCATCATGCACCGCCGGGTGCAGGGAATGCTCCAAGATCATCGTAGA-3'<br>3'-CTAAGTAGTACGTGGCGGCCCACGTCCCTTACGAGGTTCTAGTAGCATCTTCGA-5' |
| 1I | Arg146->Lys | Site-directed Priming | 5'-GGGGCTACAAGGATAGATAT-3' |
| T1 | COOH Truncation @ Trp179 | Linker Insertion | 5'-CGTGGTAATGATAGA-3'<br>3'-CATTACTATCTTCGA-5' |

*Designation

TABLE 2

ADP-RIBOSYLTRANSFERASE ACTIVITIES OF RECOMBINANT CTXA1 ANALOGS[1]

| CTX MOLECULE | MUTATION | PROTEIN ADDED TO ASSAY($\mu$G)[2] | SPECIFIC ACTIVITY FOR HEM G. PROTEIN[3] |
|---|---|---|---|
| Commercial CTXA1 (without urea) | none | 1.00 | 1.00 |
| Commercial CTXA1 (with urea) | none | 1.11 | 0.53 |
| rCTXA1/A7 | none | 1.56 | 0.56 |
| rCTXA1/L7 | Arg7->Lys | 1.46 | 0 |
| rCTXA1/1B | His44->Asn | 1.47 | 0 |
| rCTXA1/1C | His70->Asn | 1.51 | 0.05 |
| rCTXA1/1D | Glu112->Gln | 1.65 | 0 |
| rCTXA1/1E | Tyr6->Phe | 1.04 | 1.01 |
| rCTXA1/1F | Asp9->Glu | 0.91 | 0.10 |
| rCTXA1/1G | Pro185->Gln | 1.23 | 0.81 |
| rCTXA1/1H | Cys187->Ala | 1.14 | 0.83 |
| rCTXA1/1I | Arg146->Lys | 1.05 | 0.83 |
| rCTXA1/T1 | Truncated at Trp179 | 1.85 | <0.01 |

[1]The absolute amount of each protein used in each ADP-ribosyltransferase assay (see FIG. 4) was estimated by densitometric scanning of the stained SDS-polyacrylamide gel (FIG. 4, panel A) containing identical amounts of each protein used in the assay. The autoradiogram of the gel containing the human erythrocyte membranes (FIG. 4, Panel C) was subsequently scanned to determine the radiographic density of the G protein alpha subunit ribosylated by each CTXA1 protein preparation. The density of the G protein band resulting from ADP-ribosylation with commercial CTXA1 without added urea was taken as 1.00 and the density of the band resulting form ribosylation by the other CTXA1 proteins was related to this preparation as a percentage of its density. These fractions were then normalized to 1.00 $\mu$g of added CTXA1 protein based on the densitometric of the stained gel to obtain an approximate, relative specific activity.
[2]The amount of commercial CTXA1 (without added urea) in the assay was taken as 1.00 $\mu$g.
[3]The radiographic density of the G protein alpha subunit ADP-ribosylated by the commercial CTXA1 (without added urea) was taken as 1.00.

FIG. 4 shows a stained SDS-polyacrylamide gel (Panel A) of inclusion-body preparations of rCTXA1 and its site-specific analogs. An amount of protein identical to that shown in this gel was used to catalyze the individual ADP-ribosyltransferase reactions. Trichloroacetic acid (TCA) precipitates from these reactions were also run in SDS-PAGE and the gels subjected to autoradiography to illuminate the [$^{32}$P]ADP-ribose-labeled substrates. Panel B illustrates the results of the reactions without added G protein-containing human erythrocyte membrane preparation and Panel C shows the reactions with this added substrate.

The most important finding of these experiments is found in FIG. 4, Panel C (and confirmed in Panel B): certain site-specific amino acid residue substitutions result in diminishment and, in some cases, apparently complete loss of enzyme activity as measured in this assay. In this regard, rCTXA1/L7 (Arg$^9$→Lys), rCTXA1/1B (His$^{44}$→Asn) and rCTXA1/1D (Glu$^{112}$→Gln) analog subunits appear to possess virtually no enzyme activity, whereas analogs rCTXA1/1C (His$^{70}$→Asn) and rCTXA1/1F (Asp$^9$→Glu) appear to have reduced activity when compared with both native CTXA (with urea) and rCTX1/A7 (no mutation other than the methionine residue at the amino terminus). Truncation at Trp$^{179}$ (rCTXA1/T1/1156) also results in an analog A subunit with severely diminished enzyme activity.

Although these autoradiographic assays of enzyme activity are not strictly quantitative, we have attempted to derive a quantitative assessment from the gel and autoradiograms of FIG. 4 to illustrate in a numerical sense what can be visually observed. This evaluation is found in Table 2. Here, we subjected the stained SDS-polyacrylamide gel (FIG. 4, Panel A), containing rCTXA1 and each of the analogs described previously, to integrative scanning densitometry to more accurately assess the relative amount of each protein added to the assay; these were related to the amount of A1 subunit in native CTXA (without urea) added to the assay, taken as a value of 1.00 µg. Although an attempt was made to add equivalent amounts of each protein to the assays (estimated on the basis of the percentage of subunit protein in each inclusion body preparation), it can be seen that this estimation may have lacked precision. The autoradiogram of the subsequent enzyme reactions with G protein substrate (FIG. 4, Panel C) was also subjected to densitometry to determine the relative density of the radiographic image of the radiolabeled G protein a subunit band with that labeled by native CTXA (no urea) taken as 100%. An approximate-relative specific activity was then calculated by dividing the image density by the amount of added enzyme, with the specific activity of native CTX (without urea) taken as 1.00. It should be noted that the results of this type of quantitation are subject to certain experimental limitations (e.g., assumption of equal dye staining by each of the subunit preparations, band selection and circumscription for digitized densitometry, densitometer response characteristics, and assumption of a linear relationship between [$^{32}$P]ADP-ribose labelling and radiographic density). Nevertheless, the results (Table 2) illustrate in a numerical manner what can be visually observed in the autoradiograms: marked diminishment of enzyme activity in analogs rCTXA1/1C (His$^{70}$→Asn), rCTXA1/1F (Asp$^9$→Glu), and rCTXA1/T1 (Trp$^{179}$ truncation) and virtual loss of activity by analogs rCTXA1/L7 (Arg$^9$→Lsy), rCTXA1/1B (His$^{44}$→Asn), and rCTXA1/1D (Glu112→Gln).

In the case in which no exogenous substrate is added (FIG. 4, Panel B), both native CTXA and the enzymatically-active CTXA1 proteins can be seen to be autocatalytic, i.e., to catalyze the hydrolysis of NAD and the transfer of ADP-ribose to the enzyme itself (either in cis, in trans, or both). Multiple bands seen in the autoradiogram may be due to contaminating E. coli proteins capable of being ADP-ribosylated; alternatively, yet unlikely, they may represent minor variants of the subunit proteins (e.g., proteolytically-nicked or, perhaps, variants possessing some residual secondary structure in SDS). Recombinant CTXA1 preparations appear much more capable of participating in the autocatalytic process than does the A subunit of native CTX. The reasons for this increased autoribosylation are not presently understood, although it may be related to lack of substrate specificity by the yet-to-be-renatured recombinant protein, exposure of a sensitive ribosylation site in the recombinant protein as a result of improper secondary structure (no attempt was made in this particular experiment to achieve native conformation), or to the presence of ARFs (ADP-ribosylation factors) (31–37) in the crude recombinant preparations that stabilize the autocatalysis. However, when G protein substrate is added in the form of human erythrocyte membranes (Panel C), the focus of the ADP-ribosyltransferase reaction is shifted to this substrate, quenching autoribosylation.

FIG. 5 demonstrates that the same general pattern of diminishment and loss of enzyme activity seen with the rCTXA1 analogs is also observed when the same residue substitutions are made in rCTXA versions of the recombinant subunit (i.e., versions with the A2 "tail" still covalently linked). However, the presence of the A2 region appears to significantly reduce the ADP-ribosyltransferase of the enzymatically-active proteins. This reduction is more clearly illustrated in FIG. 6, in which identical amounts of rCTXA and rCTXA1 are evaluated in the enzyme assay (Panel A), the radiolabeled products run on the same gel, and consequently subjected to equivalent autoradiographic exposure times (Panel B). As can be seen, rCTXA1 appears to possess greater activity than rCTXA (compare lanes 7 and 4). Again, neither subunit construction with the Arg$^9$→Lys substitution (lanes 5 and 8) possess measurable ADP-ribosyltransferase activity for the G protein substrate. That this loss of enzyme activity in the analogs is not the result of E. coli contaminants suppressing catalysis is evident by the ability of native CTXA to ribosylate G protein in the presence of the E. coli-produced, analog-containing preparations (lanes 6 and 9).

Because of their reduction or essential elimination of a major marker of toxic activity (ADP-ribosyltransferase), the recombinant CTXA1 analog molecules produced by clones pCTXA1/L7/1156, pCTXA1/1B/1156, pCTXA1/1C/1156, pCTXA1/1D/1156, pCTXA1/1F/1156, and pCTXA1/T1/1156, as well as their rCTXA analog counterparts, are anticipated to have application alone or in combination with CTXB in safer vaccines. The described mutations would not be expected to reduce the normal, protective, immunogenic properties of native CTX subunits. The CTXA and CTXA1 analogs of this invention thus have application in combination with CTXB subunits in the form of a holotoxoid. The CTXB subunits may augment the immune response to CTXA and CTXA1, and vice-versa, and each may have protective epitopes. The CTXB subunits can be derived from V. cholerae or can be genetically-engineered subunits and their analogs. Genetically-engineered subunit products can include fusion proteins and non-fusion proteins.

IN VITRO ASSOCIATION OF rCTX SUBUNITS

A number of methods by which native cholera toxin can be dissociated and the individual subunits reassociated in vitro to reform the holotoxin molecules have been described in the literature(36,37). In vitro reassociation of the subunits of pertussis toxin has also been described in the literature for native subunits(38–40). Using a similar procedure, recombinant CTX subunits can be isolated, associated in vitro to form holotoxin-like species, and purified. In general, following expression and recovery, the individual subunits are combined in stoichiometric ratios (based on their relative content of specific subunit protein, if in the form of inclusion body preparations), approximating the ratio of subunits found in native CTX holotoxin. The preparation is solubilized in an aqueous solution containing a chaotropic agent or a detergent, or both. The preparation is subjected to reducing conditions (generally a reducing agent or a hydrogen atmosphere, or both) and then oxidized (with either an oxidizing agent or under an oxygen-enriched atmosphere, or both) to reform the necessary intramolecular disulfide bridges. Association of the subunits into holotoxin-like species is accomplished by diminishment or removal of the chaotropic or detergent solubilizing agent. This can be accomplished by a variety of means, to include filtration and buffer exchange by dialysis chromatography. The holotoxin-like species are then purified by conventional means, e.g., ion exchange, size-exclusion and affinity chromatography. It should be noted that B multimeric species, without the A subunit, may be recovered by similar means if inclusion-body preparations of the latter subunit are not added.

The genetically engineered analog subunits of this invention can be formulated, in a conventional manner, into a toxoided cholera vaccine. In the case of a toxin that has been "genetically" inactivated, such as cholera toxin in the present invention, further inactivating steps (such as chemical treatment or heat treatment) should not usually be required since these products are produced in non-pathogenic organisms and are inherently free of the enzyme activities that are generally accepted to elicit the adverse reactions to whole-cell cholera vaccines. Nevertheless, it is necessary to control purity of the recombinant product, particularly with regard to the endotoxin content. In general, recombinant holotoxoid, recombinant holotoxoid-like macromolecules, recombinant B subunit macromolecules, recombinant B subunit alone or possibly B subunit recombinant analogs, and even A subunit analogs alone described in the present invention as potential vaccinating antigens would be purified to $\geq 90\%$ homogeneity. The nature and estimated quantity of contaminants, if any, would be evaluated to ensure that the extent of endotoxin contamination meets the standards of the individual regulatory agencies.

For purposes of parenteral delivery, the vaccine materials would normally be adsorbed onto aluminum adjuvants. This can be accomplished by at least two means: precipitation with preformed alum and precipitation with aluminum salts. The adsorbed precipitates are then resuspended in an excipient to yield a dosage concentration of vaccine antigen generally in the range of 5–100 μg per dose and an alum amount usually not exceeding 1.5 mg/dose; volume per dose is in the range of 0.1–1.0 ml. The suspending excipient is commonly a buffered solution (e.g., phosphate-buffered saline, pH 7.0), may have added stabilizers (e.g., glycerol), and will likely contain a preservative (e.g., 0.01% Thimerosal) to prevent microbial contamination and to extend shelf life.

The formulation and delivery of recombinant cholera toxoid, or subcomponents thereof, via live vector systems as also encompassed within this invention will depend upon the nature of that system. For example, oral delivery of recombinant (mutant) V. cholerae, Salmonella sp., vaccinia virus, or adenovirus carrying genes for the A or A and B subunits, might well be encapsulated in enteric-coated delivery vehicles for passage to the gut or in aerosolizable forms (e.g., with liposomes) for targeting to the respiratory tract in order to elicit secretory immunoglobulin A antibodies for protection at mucosal surfaces. Alternatively, other oral forms of the vaccine can be prepared in accordance with procedures described in the literature, suitably adapted to accommodate the present antigenic agents. For instance, a recombinant V. cholerae strain can be lyophilized and mixed with a bicarbonate buffer to neutralize gastric acidity(41); or a holotoxoid in accordance with this invention can be used in the form of an effervescent tablet, appropriately buffered, to supplement a killed, whole-cell vaccine(l).

While this invention has been specifically illustrated in relation to recombinant production in E. coli, it will be appreciated by those skilled in the art that the principles for mutagenesis of the analog subunits as described herein may be employed in connection with other recombinant hosts and expression systems, and to produce other inactivated analogs of the toxin. Further, it should be understood that assembly of mutant analogs into a holotoxoid can take place in intact cells via homologous recombination, e.g., in V. cholerae, rather than in vitro. It is intended that the present invention include all modifications and improvements as come within the scope of the present invention as claimed.

BIBLIOGRAPHY

1. Holmgren, J. et al. (1989) Vaccine 7:94–96.
2. Long A. R., Los Angeles Times, Apr. 21, 1991, A1-A5.
3. Levine, M. M. et al. (1983) Microbiol. Rev., 47:510–550.
4. Pierce, N. F. et al. (1985) Infect. Immun. 50:813–816.
5. Finkelstein, R. A. (1988) in Immunochemical and molecular genetics of Bacterial pathogens (Owen P. and Foster T. J., eds.), pp. 85–102, Elsevier Science Publishers, North Holland, The Netherlands.
6. Fishman, P. H. (1990) in ADP-Ribosylating Toxins and G Proteins, (Moss J. and Vaughan M. eds.) pp. 127–140, American Society for Microbiology, Washington D.C.
7. U.S. Pat. No. 4,666,837 (Harford et al.).
8. U.S. Pat. No. 4,328,209 (Honda et al.)
9. Kaper, J. B. et al. (1984) Nature 308:655–658.
10. U.S. Pat. No. 4,751,064 (Sela et al.).
11. Black, R. E. et al. (1987) Infect. Immun. 55:1116–1120.
12. Spriggs, D. R., and Sack, R. B. (1990) J. Inf. Dis. 162:584–590.
13. Kaper, J. B., and Levine, M. M. (1990) Res. Microbiol. 141:901–906.
14. Duffey, L. K. et al. (1981) FEBS Lett. 126:187–190.
15. Mekalanos, J. J. et al. (1979) J. Biol. Chem. 254:5855–5861.
16. Mekalanos, J. J. (1983) Nature 306:551–557.
17. Yamamoto, T. et al. (1984) FEBS Lett. 169:241–246.
18. Matteuci, M. D., and Caruthers, M. H. (1981) J. Am. Chem. Soc. 103:3185ff.
19. Bachmann, B. J. et al. (1976) Bacteriol. Rev. 40:116–167.
20. Sussman, R., and Jacob, F. (1962) C. R. Acad. Sci; 254:1517–1579.
21. Sambrook, J. et al. (1989) Molecular cloning: a laboratory manual, 2nd Edition, Cold Spring Harbor Laboratory Press, Cold Spring Harbor, N.Y.
22. Sanger, F. et al. (1977) Proc Natl. Acad. Sci., USA 74:5463–5467.
23. Heidecker, G. et al. (1980) Gene 10:69–73.
24. Hewick, R. M. et al. (1981) J. Biol. Chem. 256:7990–7997.

25. Hunkapillar, M. W. et al. (1983) *Meth. Enzymol.* 91:399–413.
26. Laemmli, U.K. (1970) *Nature* 227:680–685.
27. Hunkapillar, M. W. et al., supra, at pp. 227–236.
28. Kaslow, H. R. et al. (1980) *J. Biol. Chem.* 255:3786–3741.
29. Fling, S. P., and Gregerson, D. S. (1986) *Anal. Biochem.* 155:83–88.
30. Burnette, W. N. et al. (1988) *Science* 242:72–74.
31. Kahn, R. A., and Gilman, A. G. (1984) *J. Biol. Chem.* 259:6228–6234.
32. Kahn, R. A. and Gilman, A. G. (1986) *J. Biol. Chem.* 261:7906–7911.
33. Tsai, S.-C. et al. (1987) *Proc. Natl. Acad. Sci., USA* 84:5139–5142.
34. Tsai, S.-C. et al. (1988) *J. Biol. Chem.* 263:1768–1772.
35. Bovak, D. A. et al. (1990) *Biochemistry* 29:855–861.
36. Hardy, S. J. S. et al. (1988) *Proc. Natl. Sci., USA* 85:7109–7113.
37. Finkelstein, R. A. et al. (1974) *J. Immunol.* 113:145–150.
38. Tamura, M. et al. (1982) *Biochem.* 21:5516–5522.
39. Bartley, T. D. et al. (1989) *Proc. Natl. Acad. Sci., USA* 86:8353–8357.
40. Yamakawa, Y. et al. (1990) *Anal. Biochem.* 185:176–181.
41. Cryz, S. J. et al. (1990) *Vaccine* 8:577–580.

What is claimed:

1. A modified cholera toxin having reduced or essentially no catalytic activity associated with cholera toxin reactogenicity, in which the modification comprises the substitution of a different amino acid in one or more of the sites in the native sequence for mature catalytic subunit A, aa 19-258 of SEQ ID NO: 2 selected from among arginine-7, aspartic acid-9, histidine-44, histidine-70 and glutamic acid-112 or a truncation of the carboxyl-terminal portion of said sequence beginning at the amino acid immediately following tryptophan-179.

2. The modified cholera toxin of claim 1, which is capable of eliciting a cholera toxin-neutralizing immune response.

3. The modified cholera toxin of claim 1, which is obtained by site-specific mutagenesis resulting in a mutation of catalytic subunit A which is less active or essentially inactive as determined by assay of ADP-ribosyltransferase activity.

4. The modified cholera toxin of claim 1 which includes B oligomer.

5. An improved anti-cholera vaccine comprising an effective amount of modified cholera toxin which can elicit a cholera toxin-neutralizing immune response and has reduced or essentially no catalytic activity associated with cholera toxin reactogenicity, wherein the modification comprises the substitution of a different amino acid in one or more of the sites in the native sequence for mature catalytic subunit A, aa 19-258 of SEQ ID NO: 2 selected from among arginine-7, aspartic acid-9, histidine-44, histidine-70 and glutamic acid-112 or a truncation of the carboxyl-terminal portion of said sequence beginning at the amino acid immediately following tryptophan-179.

6. The improved vaccine of claim 5, wherein the toxin-neutralizing immune response provides immunoprotection against cholera disease.

7. The improved vaccine of claim 5, wherein the modified cholera toxin has been derived by site-specific mutagenesis resulting in a mutation of catalytic subunit A which has less or essentially no ADP-ribosyltransferase activity.

8. The improved vaccine of claim 5, wherein the modified cholera toxin includes B oligomer (SEQ ID NO: 4).

* * * * *

UNITED STATES PATENT AND TRADEMARK OFFICE
CERTIFICATE OF CORRECTION

PATENT NO. : 5,770,203
DATED : JUNE 23, 1998
INVENTOR(S) : BURNETTE, et al.

It is certified that error appears in the above-identified patent and that said Letters Patent is hereby corrected as shown below:

Column 1, line 9, prior to Background of the Invention, Insert the following statement:

-- This invention was made in part with Government support under NIH Grant No. 2 R01-AI2432000651. The Government may have certain rights in the invention. --

Signed and Sealed this

Eleventh Day of April, 2000

Attest:

Attesting Officer

Q. TODD DICKINSON

Director of Patents and Trademarks

UNITED STATES PATENT AND TRADEMARK OFFICE
CERTIFICATE OF CORRECTION

PATENT NO.   : 5,770,203

DATED        : June 23, 1998

INVENTOR(S)  : W. Neal Burnette and Harvey R. Kaslow

It is certified that error appears in the above-identified patent and that said Letters Patent is hereby corrected as shown below:

Column 2, Line 29:  Change "Figure 1A" to -- Figure 1A-1A-3 --
Column 2, Line 29:  Insert -- sequence -- before "(SEQ ID NO: 1)", delete "sequencer"
Column 2, Line 41:  Change "Figure 1B" to -- Figure 1B-1B-1 --
Column 3, Line 55:  Change "Panel A" to -- Figure 4A --
Column 3, Line 65:  Change "Panel" to -- Figure --
Column 4, Line 2:   Change "Panel" to -- Figure --
Column 4, Line 11:  Change "FIGS. 4A-4C" to -- Figure 4 --
Column 4, Line 13:  Change "FIGS. 6A&6B" to -- Figure 6 --
Column 4, Line 16:  Change "(Panel A)" to --(Figure 5A) --
Column 4, Line 16:  Change "Panel 5A" to – Figure 5A --
Column 4, Line 18:  Change "Figure 4, Panel A" to -- Figure 4A --
Column 4, Line 21:  Change "(Panel 5B)" to – (Figure 5B) --
Column 4, Line 23:  Change "(Panel 5C)" to – (Figure 5C) --
Column 4, Line 32:  Change "Panel 6A" to --Figure 6A--.
Column 4, Line 33:  Change "Panel 6B" to --Figure 6B--.
Column 4, Line 64:  Change "1A" to -- 1A-1C --
Column 8, Line 57:  Change "1 and 2" to -- 1A-1A-3 and 2 --
Column 9, Line 52:  Change "CTXA and CTXA" to -- CTXA and CTXA1 --
Column 11, Line 50: Change "/L$^7$/" to -- /L7/ --
Column 11, Line 51: Change "/L$^7$/" to -- /L7/ --
Column 11, Line 62: Insert -- were -- before "synthesized"
Column 12, Line 6:  Insert -- Glu -- after "→" (2nd occurrence).
Column 12, Line 13: Change "18$^7$" to -- 187 --
Column 13, Line 32: Change "Arg146" to -- Arg$^{146}$ --
Column 14, Line 24: Change "Analoa" to -- Analog --
Column 16, Lines 13-14:  Change "Figs. 4, 5 and 6" to -- Figs. 4A-4C, 5A-5C and 6A-6B --

UNITED STATES PATENT AND TRADEMARK OFFICE
CERTIFICATE OF CORRECTION

PATENT NO. : 5,770,203

DATED : June 23, 1998

INVENTOR(S) : W. Neal Burnette and Harvey R. Kaslow

It is certified that error appears in the above-identified patent and that said Letters Patent is hereby corrected as shown below:

Column 17, Line 1: Change "Figure 4" to -- Figure 4A-4C --
Column 17, Line 1: Change "(Panel A)" to -- (Figure 4A) --
Column 17, Line 8: Change "Panel B" to -- Figure 4B --
Column 17, Line 11: Change "Panel C" to -- Figure 4C --
Column 17, Line 14: Change "Figure 4, Panel C" to -- Figure 4C --
Column 17, Line 14: Change "Panel B" to -- Figure 4B --
Column 17, Line 30: Change "Figure 4" to -- Figure 4A-4C --
Column 17, Lines 32-33: Change "(Figure 4, Panel C)" to -- (Figure 4C) --
Column 17, Line 44: Change "(FIG. 4, Panel A) to --(Figure 4A)--.
Column 17, Line 46: Change "a" to -- $\alpha$ --
Column 17, Line 63: Change "Lsy" to -- Lys --
Column 17, Line 64: Change "Glu112" to -- $Glu^{112}$ --
Column 17, Lines 66: Change "(Figure 4, Panel B)" to -- (Figure 4B) --
Column 18, Line 21: Change "(Panel C)" to -- (Figure 4C) --
Column 18, Line 24: Change "Figure 5" to -- Figure 5A-5C --
Column 18, Line 32: Change "Figure 6" to -- Figure 6A-6B --
Column 18, Line 33: Change "(Panel A)" to -- (Figure 5A) --
Column 18, Line 36: Change "(Panel B)" to – (Figure 5B) --

UNITED STATES PATENT AND TRADEMARK OFFICE
CERTIFICATE OF CORRECTION

PATENT NO. : 5,770,203
DATED : June 23, 1998
INVENTOR(S) : W. Neal Burnette and Harvey R. Kaslow It is certified that error appears in the above-identified patent and that said Letters Patent is hereby corrected as shown below:

Column 1,
Line 9, prior to "Background of the Invention", insert the following statement:

-- This invention was made in part with Government support under NIH Grant No. 2 RO1-AI 2432000651. The Government may have certain rights in the invention. --

Signed and Sealed this

Second Day of October, 2001

Attest:

*Nicholas P. Godici*

NICHOLAS P. GODICI
*Attesting Officer*    *Acting Director of the United States Patent and Trademark Office*